United States Patent
Oestergaard et al.

(10) Patent No.: US 7,588,926 B2
(45) Date of Patent: *Sep. 15, 2009

(54) PROTEASES

(75) Inventors: Peter Rahbek Oestergaard, Virum (DK); Leonardo De Maria, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 146 days.

This patent is subject to a terminal disclaimer.

(21) Appl. No.: 10/544,861

(22) PCT Filed: Feb. 9, 2004

(86) PCT No.: PCT/DK2004/000090

§ 371 (c)(1),
(2), (4) Date: Aug. 5, 2005

(87) PCT Pub. No.: WO2004/072221

PCT Pub. Date: Aug. 26, 2004

(65) Prior Publication Data

US 2006/0147499 A1    Jul. 6, 2006

Related U.S. Application Data

(60) Provisional application No. 60/510,411, filed on Oct.

(Continued)

(30) Foreign Application Priority Data

| Feb. 7, 2003 | (DK) | 2003 00173 |
| Mar. 20, 2003 | (DK) | 2003 00426 |
| Jun. 19, 2003 | (DK) | 2003 00912 |
| Jun. 19, 2003 | (DK) | 2003 00913 |
| Jun. 19, 2003 | (DK) | 2003 00914 |
| Jun. 19, 2003 | (DK) | 2003 00915 |
| Oct. 10, 2003 | (DK) | 2003 01492 |
| Oct. 10, 2003 | (DK) | 2003 01493 |

(51) Int. Cl.
C12N 9/58 (2006.01)
C12N 15/57 (2006.01)
C12N 15/74 (2006.01)
C12N 15/79 (2006.01)
C11D 3/386 (2006.01)
A23K 1/165 (2006.01)

(52) U.S. Cl. .................. 435/223; 435/69.1; 435/252.3; 435/320.1; 536/23.2; 510/306; 423/53

(58) Field of Classification Search .................. None
See application file for complete search history.

(56) References Cited

U.S. PATENT DOCUMENTS 3,683,069 A    8/1972    Hooreman (Continued)

FOREIGN PATENT DOCUMENTS

DE    2004328    9/1981

(Continued)

OTHER PUBLICATIONS

Screen et al., Journal of Biological Chemistry, vol. 275, No. 9, pp. 6689-6694 (2000).

(Continued)

*Primary Examiner*—Nashaat T Nashed
*Assistant Examiner*—William W Moore
(74) *Attorney, Agent, or Firm*—Elias J. Lambiris

(57) ABSTRACT

The invention relates to a novel class of serine proteases of peptidase family S2A or S1E that are stable in the presence of copper (Cu2+) and/or inhibited by copper only to a limited extent. Structural features of potential relevance for this effect are also disclosed. This class of proteases includes proteases derived from *Brachysporiella gayana, Nocardiopsis dassonvillei* subsp. *dassonvillei, Nocardiopsis prasina*, and *Nocardiopsis alba*. The invention also relates to DNA encoding such proteases and the expression thereof in a host cell, animal and plant cells, as well as to the use thereof in animal feed and in detergents. In particular, the invention relates to animal feed and animal feed additives, such as premix, incorporating these proteases together with 1-500 ppm Cu (in-feed-concentration).

24 Claims, 1 Drawing Sheet

```
                 10        18        28        38        48                    SEQ ID NO:
         ADIIGGLAYT MG--GRCSVG FAATNAAGQP GFVTAGHCGR VGTQVTIGNG  Protease 10       2
         ATVQGGDVYY INRSSRCSIG FAVTT----- GFVSAGHCGG SGASATTSSG  Metarhizium      4
         ADIIGGLAYT MG--GRCSVG FAATNAAGQP GFVTAGHCGR VGTQVSIGNG  Protease 11       6
         ADIIGGLAYT MG--GRCSVG FAATNAAGQP GFVTAGHCGR VGTQVTIGNG  Protease 35       8
         ADIIGGLAYT MG--GRCSVG FAATNASGQP GFVTAGHCGT VGTPVSIGNG  Protease 08      10
         ADIIGGLAYY MG--GRCSVG FAATNSAGQP GFVTAGHCGT VGTGVTIGNG  Protease 18      12
         --ILGGDPFV INNSAVCSVG FAVSG----- GFVSAGHCGG QGSPVTYIDG  Brachysporiella  14

56        65        75        85        95
         --RGVFEQSV FPG-NDAAFV RGTSNFTLTN LVSRYNTGGY ATVAGHNQAP  Protease 10
         BALGTPSGSV FPGSADMAYV RTVSGTVLRG YINGYGQGSF P-VSGSSEAA  Metarhizium
         --QGVFEQSI FPG-NDAAFV RGTSNFTLTN LVSRYNTGGY ATVAGHNQAP  Protease 11
         --RGVFEQSI FPG-NDAAFV RGTSNFTLTN LVSRYNTGGY ATVAGHNQAP  Protease 35
         --QGVFERSV FPG-NDSAFV RGTSNFTLTN LVSRYNTGGY ATVSGSSQAA  Protease 08
         --TGTFQNSV FPG-NDAAFV RGTSNFTLTN LVSRYNSGGY QSVTGTSQAP  Protease 18
         GALGTIEGSV FPGDADMSFI RAVDGTDLPG IVGTYGNGDQ P-IPGSNVAP  Brachysporiella 105       115       125       135       145
         IGSSVCRSGS TTGWHCGTIQ ARGQSVSYPE GTVTNMTRTT VCAEPGDSGG  Protease 10
         VGASICRSGS TTQVHCGTIG AKGATVNYPQ GAVSGLTRTS VCAEPGDSGG  Metarhizium
         IGSSVCRSGS TTGWHCGTIQ ARGQSVSYPE GTVTNMTRTT VCAEPGDSGG  Protease 11
         IGSSVCRSGS TTGWHCGTIQ ARGQSVSYPE GTVTNMTRTT VCAEPGDSGG  Protease 35
         IGSQICRSGS TTGWHCGTVQ ARGQTVSYPQ GTVQNLTRTN VCAEPGDSGG  Protease 08
         AGSAVCRSGS TTGWHCGTIQ ARNQTVRYPQ GTVYSLTRTN VCAEPGDSGG  Protease 18
         IGSSVCRSGT TTGYHCGQLD AYDVTVNYDV GPVFGLTMTS ACAEPGDSGG  Brachysporiella 155       165       175       185
         SYISGTQAQG VTSGGSGNCR TGGTTFYQEV TPMVNSWGVR LRT-  Protease 10
         SFYSGSQAQG VTSGGSGDCS RGGTTYFQPV NRILQTYGLT LVTA  Metarhizium
         SYISGNQAQG VTSGGSGNCR TGGTTFYQEV TPMVNSWGVR LRT-  Protease 11
         SYISGNQAQG VTSGGSGNCR TGGTTFYQEV TPMVNSWGVR LRT-  Protease 35
         SFISGSQAQG VTSGGSGNCS FGGTTYYQEV NPMLSSWGLT LRT-  Protease 08
         SFISGSQAQG VTSGGSGNCS VGGTTYYQEV TPMINSWGVR IRT-  Protease 18
         SFFAGDQAQG VTSGGSGDCT SGGQTFFQPV NEILETYGLS LTTA  Brachysporiella
```

Related U.S. Application Data

(60) 10, 2003, provisional application No. 60/510,406, filed on Oct. 10, 2003, provisional application No. 60/480,107, filed on Jun. 20, 2003, provisional application No. 60/480,102, filed on Jun. 20, 2003, provisional application No. 60/480,096, filed on Jun. 20, 2003, provisional application No. 60/480,024, filed on Jun. 20, 2003, provisional application No. 60/456,470, filed on Mar. 21, 2003, provisional application No. 60/445,686, filed on Feb. 7, 2003.

(56) References Cited

U.S. PATENT DOCUMENTS

| | | | |
|---|---|---|---|
| 3,723,250 | A | 3/1973 | Aunstrup et al. |
| 3,823,072 | A | 7/1974 | Hooreman |
| 3,868,448 | A | 2/1975 | Hahn et al. |
| 3,966,971 | A | 6/1976 | Morehouse et al. |
| 4,073,884 | A | 2/1978 | Hartdegen et al. |
| 4,518,697 | A | 5/1985 | Bartnik et al. |
| 5,047,240 | A | 9/1991 | Hooreman |
| 5,312,748 | A | 5/1994 | Liu et al. |
| 5,646,028 | A | 7/1997 | Leigh |
| 5,705,379 | A | 1/1998 | Wilson et al. |
| 5,811,382 | A | 9/1998 | Damhus et al. |
| 6,855,548 | B2 | 2/2005 | Sjoeholm et al. |
| 7,179,630 | B2 * | 2/2007 | Lassen et al. ............ 435/212 |
| 2006/0143738 | A1 * | 6/2006 | Lassen .................... 800/288 |
| 2006/0147499 | A1 * | 7/2006 | Oestergaard et al. ....... 424/442 |
| 2006/0236414 | A1 * | 10/2006 | Lassen ..................... 800/14 |
| 2007/0104764 | A1 * | 5/2007 | Jensen et al. ............. 424/442 |

FOREIGN PATENT DOCUMENTS

| | | |
|---|---|---|
| EP | 0 130 756 | 1/1985 |
| EP | 0 300 466 | 1/1989 |
| EP | 0 506 448 | 9/1992 |
| EP | 0 647 710 | 4/1995 |
| EP | 0 897 985 | 2/1999 |
| JP | 2255081 | 10/1990 |
| JP | 2003284571 | 10/2003 |
| WO | WO 88/03947 | 6/1988 |
| WO | WO 91/10723 | 7/1991 |
| WO | WO 95/02044 | 1/1995 |
| WO | WO 95/21540 | 6/1995 |
| WO | WO 95/28850 | 11/1995 |
| WO | WO 96/05739 | 2/1996 |
| WO | WO 98/56260 | 12/1998 |
| WO | WO 99/53038 | 10/1999 |
| WO | WO 01/58276 | 8/2001 |
| WO | WO 2004/070106 | 8/2004 |
| WO | WO 2004/072221 | 8/2004 |
| WO | WO 2004/072279 | 8/2004 |
| WO | WO 2004/111219 | 12/2004 |
| WO | WO 2004/111220 | 12/2004 |
| WO | WO 2004/111221 | 12/2004 |
| WO | WO 2004/111222 | 12/2004 |
| WO | WO 2004/111223 | 12/2004 |

OTHER PUBLICATIONS

Lao et al., Applied and Environmental Microbiology, vol. 62, No. 11, pp. 4256-4259 (1996).
Dixit et al., Biochimica, vol. 1523, pp. 261-268 (2000).
Merops XP-002285393 (2004).
Caine et al., Animal Feed Science Technology, vol. 71, pp. 177-183 (1998).
Gill et al., Analytical Biochemistry, vol. 182, pp. 319-326 (1989).
Michalik et al., Ukr. Biokhim. Zh., vol. 69, No. 3, pp. 28-38 (1997) Abstract only.
Needleman et al., Journal of Molecular Biology, vol. 48, pp. 443-453 (1970).
Refstie et al, Aquaculture, vol. 162, pp. 301-312 (1998).
Smith et al., Analytical Biochemistry, vol. 150, pp. 76-85 (1985).
Altschul et al., SEQ ID No. 2 Serine Proteinase, GenPept, Acess PQ0104 (1997).
MEROPS Database, Alignment of Subfamily S1E peptidases (2004).
Sidhut et al., The Journal of Biological Chemistry, vol. 269, No. 31, pp. 20167-20171 (1994).
Henderson et al., Journal of Bacteriology, vol. 169, No. 8, pp. 3778-3784 (1987).
Mitsuiki et al., Bioscience Biotechnol Biochemistry, vol. 66, No. 1, pp. 164-167 (2002).
Sequence Alignment with protease disclosed in EP 506446, Derwent GeneSeq Nucleotide, accession No. AAQ29011 (2004).
Gayle et al., The Journal of Biological Chemistry, vol. 268, No. 29, pp. 22105-22111 (1993).
Whistock et al., Quarterly Reviews of Biophysics, vol. 36, No. 3, pp. 307-340 (2003).
Sequence Alignment of protein disclosed in PCT/DK96/00013, Accession AAW92997 (1999).
Sequence Alignment of protein disclosed in WO 2001/58276, Accession No. AAU07125 (2003).
Sequence Alignment of protein disclosed in PCT/DK96/00013, Accession No. AAX22316 (1999).
Tsujibo et al., Journal of Applied Bacteriology, vol. 69, No. 4, pp. 520-529 (1990).
Tsujibo et al., Agric Biol. Chem. vol. 54 No. 8, pp. 2177-2179 (1990).
Sequence Alignment with protease disclosed in EP 506448, Derwent GeneSeq Nucleotide, accession No. AAQ29011 (2004).
Tsujibo et al., Applied and Environmental Microbiology, vol. 69. No. 2, pp. 894-900 (2003).
O Fagain. Enzyme and Microbiol Technology, vol. 33, pp. 137-149 (2003).
Database EMBL, Accession No. AY151208, "Nocardiopsis sp. TOA-1 serine protease (napA) gene. complete cds." XP-002308395 (May 16, 2004).
Mitsuiki et al., Enzyme and Microbiol Technology, vol. 34, pp. 482-489 (2004).
Kim et al., Korean Biochemical Journal, vol. 26, No. 1, pp. 81-85 (1993).
Moriera et al., World Journal of Microbiology & Biotechnology, vol. 18, pp. 307-312 (2002).
Higgins et al., Gene, pp. 237-244 (1988), vol. 73.
Kaneda et al., Journal of Biochemistry, vol. 78, pp. 1287-1296 (1975).
Barrett et al., Handbook of Proteolytic Enzymes (1998), pp. 3 and 4.

* cited by examiner

```
                                                                        SEQ ID NO:
         10         18         28         38         48
ADIIGGLAYT MG--GRCSVG FAATNAAGQP GFVTAGHCGR VGTQVTIGNG   Protease 10      2
ATVQGGDVYY INRSSRCSIG FAVTT----- GFVSAGHCGG SGASATTSSG   Metarhizium      4
ADIIGGLAYT MG--GRCSVG FAATNAAGQP GFVTAGHCGR VGTQVSIGNG   Protease 11      6
ADIIGGLAYT MG--GRCSVG FAATNAAGQP GFVTAGHCGR VGTQVTIGNG   Protease 35      8
ADIIGGLAYT MG--GRCSVG FAATNASGQP GFVTAGHCGT VGTPVSIGNG   Protease 08     10
ADIIGGLAYY MG--GRCSVG FAATNSAGQP GFVTAGHCGT VGTGVTIGNG   Protease 18     12
--ILGGDPFV INNSAVCSVG FAVSG----- GFVSAGHCGG QGSPVTYIDG   Brachysporiella 14

56         65         75         85         95
--RGVFEQSV FPG-NDAAFV RGTSNFTLTN LVSRYNTGGY ATVAGHNQAP   Protease 10
EALGTFSGSV FPGSADMAYV RTVSGTVLRG YINGYGQGSF P-VSGSSEAA   Metarhizium
--QGVFEQSI FPG-NDAAFV RGTSNFTLTN LVSRYNTGGY ATVAGHNQAP   Protease 11
--RGVFEQSI FPG-NDAAFV RGTSNFTLTN LVSRYNTGGY ATVAGHNQAP   Protease 35
--QGVFERSV FPG-NDSAFV RGTSNFTLTN LVSRYNTGGY ATVSGSSQAA   Protease 08
--TGTFQNSV FPG-NDAAFV RGTSNFTLTN LVSRYNSGGY QSVTGTSQAP   Protease 18
GALGTIEGSV FPGDADMSFI RAVDGTDLPG IVGTYGNGDQ P-IFGSNVAP   Brachysporiella 105        115        125        135        145
IGSSVCRSGS TTGWHCGTIQ ARGQSVSYPE GTVTNMTRTT VCAEPGDSGG   Protease 10
VGASICRSGS TTQVHCGTIG AKGATVNYPQ GAVSGLTRTS VCAEPGDSGG   Metarhizium
IGSSVCRSGS TTGWHCGTIQ ARGQSVSYPE GTVTNMTRTT VCAEPGDSGG   Protease 11
IGSSVCRSGS TTGWHCGTIQ ARGQSVSYPE GTVTNMTRTT VCAEPGDSGG   Protease 35
IGSQICRSGS TTGWHCGTVQ ARGQTVSYPQ GTVQNLTRTN VCAEPGDSGG   Protease 08
AGSAVCRSGS TTGWHCGTIQ ARNQTVRYFQ GTVYSLTRTN VCAEPGDSGG   Protease 18
IGSGVCRSGT TTGYHCGQLD AYDVTVNYDV GPVFGLTMTS ACAEPGDSGG   Brachysporiella 155        165        175        185
SYISGTQAQG VTSGGGSGNCR TGGTTFYQEV TPMVNSWGVR LRT-        Protease 10
SFYSGSQAQG VTSGGGSGDCS RGGTTYFQPV NRILQTYGLT LVTA        Metarhizium
SYISGNQAQG VTSGGGSGNCR TGGTTFYQEV TPMVNSWGVR LRT-        Protease 11
SYISGNQAQG VTSGGGSGNCR TGGTTFYQEV TPMVNSWGVR LRT-        Protease 35
SFISGSQAQG VTSGGGSGNCS FGGTTYYQEV NPMLSSWGLT LRT-        Protease 08
SFISGSQAQG VTSGGGSGNCS VGGTTYYQEV TPMINSWGVR IRT-        Protease 18
SFFAGDQAQG VTSGGGSGDCT SGGQTFFQPV NEILETYGLS LTTA        Brachysporiella
```

Fig. 1

SEQUENCE LISTING

```
<160> NUMBER OF SEQ ID NOS: 14

<210> SEQ ID NO 1
<211> LENGTH: 1596
<212> TYPE: DNA
<213> ORGANISM: Nocardiopsis sp. NRRL 18262
<220> FEATURE:
<221> NAME/KEY: CDS
<222> LOCATION: (900)..(1466)

<400> SEQUENCE: 1
acgtttggta cgggtaccgg tgtccgcatg tggccagaat gccccttgc gacagggaac      60 ggattcggtc ggtagcgcat cgactccgac aaccgcgagg tggccgttcg cgtcgccacg     120
ttctgcgacc gtcatgcgac ccatcatcgg gtgaccccac cgagctctga atggtccacc     180
gttctgacgg tctttccctc accaaaacgt gcacctatgg ttaggacgtt gtttaccgaa     240
tgtctcggtg aacgacaggg gccggacggt attcggcccc gatcccccgt tgatcccccc     300
aggagagtag ggaccccatg cgaccctccc ccgttgtctc cgccatcggt acgggagcgc     360
tggccttcgg tctggcgctg tccggtaccc cgggtgccct cgcggccacc ggagcgctcc     420
cccagtcacc caccccggag gccgacgcgg tctccatgca ggaggcgctc cagcgcgacc     480 tgacctgac ctccgccgag gccgaggagc tgctggccgc ccaggacacc gccttcgagg     540
tcgacgaggc cgcggccgag gccgccgggg acgcctacgg cggctccgtc ttcgacaccg     600
agagcctgga actgaccgtc ctggtcaccg atgccgccgc ggtcgaggcc gtggaggcca     660
ccggcgccgg gaccgagctg gtctcctacg gcatcgacgg tctcgacgag atcgtccagg     720
agctcaacgc cgccgacgcc gttcccggtg tggtcggctg gtacccggac gtggcgggtg     780
acaccgtcgt cctggaggtc ctggagggtt ccggagccga cgtcagcggc ctgctcgcgg     840
acgccggcgt ggacgcctcg gccgtcgagg tgaccacgag cgaccagccc gagctctac      899 gcc gac atc atc ggt ggt ctg gcc tac acc atg ggc ggc cgc tgt tcg        947
Ala Asp Ile Ile Gly Gly Leu Ala Tyr Thr Met Gly Gly Arg Cys Ser
1               5                   10                  15 gtc ggc ttc gcg gcc acc aac gcc gcc ggt cag ccc ggg ttc gtc acc        995
Val Gly Phe Ala Ala Thr Asn Ala Ala Gly Gln Pro Gly Phe Val Thr
        20                  25                  30
```

```
gcc ggt cac tgc ggc cgc gtg ggc acc cag gtg acc atc ggc aac ggc    1043
Ala Gly His Cys Gly Arg Val Gly Thr Gln Val Thr Ile Gly Asn Gly
         35                  40                  45 agg ggc gtc ttc gag cag tcc gtc ttc ccc ggc aac gac gcg gcc ttc    1091
Arg Gly Val Phe Glu Gln Ser Val Phe Pro Gly Asn Asp Ala Ala Phe
 50                  55                  60 gtc cgc ggt acg tcc aac ttc acg ctg acc aac ctg gtc agc cgc tac    1139
Val Arg Gly Thr Ser Asn Phe Thr Leu Thr Asn Leu Val Ser Arg Tyr
 65                  70                  75                  80 aac acc ggc ggg tac gcc acg gtc gcc ggt cac aac cag gcc ccc atc    1187
Asn Thr Gly Gly Tyr Ala Thr Val Ala Gly His Asn Gln Ala Pro Ile
                 85                  90                  95 ggc tcc tcc gtc tgc cgc tcc ggc tcc acc acc ggt tgg cac tgc ggc    1235
Gly Ser Ser Val Cys Arg Ser Gly Ser Thr Thr Gly Trp His Cys Gly
                100                 105                 110 acc atc cag gcc cgc ggc cag tcg gtg agc tac ccc gag ggc acc gtc    1283
Thr Ile Gln Ala Arg Gly Gln Ser Val Ser Tyr Pro Glu Gly Thr Val
            115                 120                 125 acc aac atg acc cgg acc acc gtg tgc gcc gag ccc ggc gac tcc ggc    1331
Thr Asn Met Thr Arg Thr Thr Val Cys Ala Glu Pro Gly Asp Ser Gly
130                 135                 140 ggc tcc tac atc tcc ggc acc cag gcc cag ggc gtg acc tcc ggc ggc    1379
Gly Ser Tyr Ile Ser Gly Thr Gln Ala Gln Gly Val Thr Ser Gly Gly
145                 150                 155                 160 tcc ggc aac tgc cgc acc ggg ggc acc acc ttc tac cag gag gtc acc    1427
Ser Gly Asn Cys Arg Thr Gly Gly Thr Thr Phe Tyr Gln Glu Val Thr
                165                 170                 175 ccc atg gtg aac tcc tgg ggc gtc cgt ctc cgg acc tga tccccgcggt    1476
Pro Met Val Asn Ser Trp Gly Val Arg Leu Arg Thr
            180                 185 tccaggcgga ccgacggtcg tgacctgagt accaggcgtc cccgccgctt ccagcggcgt    1536
ccgcaccggg gtgggaccgg gcgtggccac ggccccaccc gtgaccggac cgcccggcta    1596

<210> SEQ ID NO 2
<211> LENGTH: 188
<212> TYPE: PRT
<213> ORGANISM: Nocardiopsis sp. NRRL 18262

<400> SEQUENCE: 2

Ala Asp Ile Ile Gly Gly Leu Ala Tyr Thr Met Gly Gly Arg Cys Ser
1               5                   10                  15

Val Gly Phe Ala Ala Thr Asn Ala Gly Gln Pro Gly Phe Val Thr
            20                  25                  30

Ala Gly His Cys Gly Arg Val Gly Thr Gln Val Thr Ile Gly Asn Gly
         35                  40                  45

Arg Gly Val Phe Glu Gln Ser Val Phe Pro Gly Asn Asp Ala Ala Phe
 50                  55                  60

Val Arg Gly Thr Ser Asn Phe Thr Leu Thr Asn Leu Val Ser Arg Tyr
 65                  70                  75                  80

Asn Thr Gly Gly Tyr Ala Thr Val Ala Gly His Asn Gln Ala Pro Ile
                 85                  90                  95

Gly Ser Ser Val Cys Arg Ser Gly Ser Thr Thr Gly Trp His Cys Gly
                100                 105                 110

Thr Ile Gln Ala Arg Gly Gln Ser Val Ser Tyr Pro Glu Gly Thr Val
            115                 120                 125

Thr Asn Met Thr Arg Thr Thr Val Cys Ala Glu Pro Gly Asp Ser Gly
130                 135                 140
```

```
Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185

<210> SEQ ID NO 3
<211> LENGTH: 1125
<212> TYPE: DNA
<213> ORGANISM: Metarhizium anisopliae
<220> FEATURE:
<221> NAME/KEY: CDS
<222> LOCATION: (1)..(1122)
<220> FEATURE:
<221> NAME/KEY: sig_peptide
<222> LOCATION: (1)..(54)
<220> FEATURE:
<221> NAME/KEY: mat_peptide
<222> LOCATION: (559)..(1122)

<400> SEQUENCE: 3
```

| | | | | | | | | | | | | | | | | |
|---|---|---|---|---|---|---|---|---|---|---|---|---|---|---|---|---|
| atg | gag | ctt | acc | aaa | ttt | ctt | gcc | tta | ctg | gca | gtt | atc | ctg | ccc | | 45 |
| Met | Glu | Leu | Thr | Lys | Phe | Leu | Ala | Leu | Leu | Ala | Val | Ile | Leu | Pro | | |
| -185 | | | | -180 | | | | | -175 | | | | | | | |
| gtc | gcc | tac | ggt | gca | cca | acg | cag | gcg | gca | agc | ctg | cac | ccc | cag | | 90 |
| Val | Ala | Tyr | Gly | Ala | Pro | Thr | Gln | Ala | Ala | Ser | Leu | His | Pro | Gln | | |
| | -170 | | | | | -165 | | | | | -160 | | | | | |
| att | ttg | gag | gcc | atg | aag | cgc | gac | ttg | ggg | ctg | aac | gcc | gag | cag | | 135 |
| Ile | Leu | Glu | Ala | Met | Lys | Arg | Asp | Leu | Gly | Leu | Asn | Ala | Glu | Gln | | |
| | -155 | | | | | -150 | | | | | -145 | | | | | |
| gcc | act | gtt | cgt | gtg | gcg | cgg | gag | atc | cat | gcc | acc | gat | gtt | att | | 180 |
| Ala | Thr | Val | Arg | Val | Ala | Arg | Glu | Ile | His | Ala | Thr | Asp | Val | Ile | | |
| | -140 | | | | | -135 | | | | | -130 | | | | | |
| gag | cag | ctg | cgc | agc | tca | gta | gcg | ttc | gct | ggt | gct | tgg | att | gac | | 225 |
| Glu | Gln | Leu | Arg | Ser | Ser | Val | Ala | Phe | Ala | Gly | Ala | Trp | Ile | Asp | | |
| | -125 | | | | | -120 | | | | | -115 | | | | | |
| gcg | gac | gtg | cta | tac | atc | ggc | att | act | gac | caa | gcc | ttg | gcc | gat | | 270 |
| Ala | Asp | Val | Leu | Tyr | Ile | Gly | Ile | Thr | Asp | Gln | Ala | Leu | Ala | Asp | | |
| | -110 | | | | | -105 | | | | | -100 | | | | | |
| gag | gtc | act | gct | gcc | ggc | gcc | acg | ccg | att | gtc | atg | acc | aac | agc | ctg | 318 |
| Glu | Val | Thr | Ala | Ala | Gly | Ala | Thr | Pro | Ile | Val | Met | Thr | Asn | Ser | Leu | |
| | -95 | | | | | -90 | | | | | -85 | | | | | |
| tcc | aag | ctg | gaa | aag | gcc | aag | gag | gat | ctc | gat | aag | ata | ttc | atc | ggc | 366 |
| Ser | Lys | Leu | Glu | Lys | Ala | Lys | Glu | Asp | Leu | Asp | Lys | Ile | Phe | Ile | Gly | |
| -80 | | | | -75 | | | | | -70 | | | | | -65 | | |
| cga | gcc | aac | acc | ctg | gaa | aca | tct | tcg | gac | act | agc | tct | ggc | att | gca | 414 |
| Arg | Ala | Asn | Thr | Leu | Glu | Thr | Ser | Ser | Asp | Thr | Ser | Ser | Gly | Ile | Ala | |
| | | | -60 | | | | | -55 | | | | | -50 | | | |
| tcg | tat | ttc | gtt | gat | gtc | gcc | gcc | aac | aag | ctc | gtt | ata | gag | gct | ctc | 462 |
| Ser | Tyr | Phe | Val | Asp | Val | Ala | Ala | Asn | Lys | Leu | Val | Ile | Glu | Ala | Leu | |
| | | -45 | | | | | -40 | | | | | -35 | | | | |
| gcc | gac | agt | cac | ggc | cat | gct | gag | caa | cta | gcc | gcg | cag | gtt | ggg | ctt | 510 |
| Ala | Asp | Ser | His | Gly | His | Ala | Glu | Gln | Leu | Ala | Ala | Gln | Val | Gly | Leu | |
| | | -30 | | | | | -25 | | | | | -20 | | | | |
| aca | tcc | gaa | ttc | gag | gtg | cgg | act | gtt | gag | acg | atg | ccg | act | acc | atg | 558 |
| Thr | Ser | Glu | Phe | Glu | Val | Arg | Thr | Val | Glu | Thr | Met | Pro | Thr | Thr | Met | |
| | -15 | | | | | -10 | | | | | -5 | | | | -1 | |
| gcc | acg | gtt | cag | ggt | ggt | gat | gtc | tat | tat | att | aat | aga | agc | tcc | cgc | 606 |
| Ala | Thr | Val | Gln | Gly | Gly | Asp | Val | Tyr | Tyr | Ile | Asn | Arg | Ser | Ser | Arg | |
| 1 | | | | 5 | | | | | 10 | | | | | 15 | | |

```
tgc tct atc ggt ttc gca gta acc aca ggt ttc gtg tcc gct gga cac     654
Cys Ser Ile Gly Phe Ala Val Thr Thr Gly Phe Val Ser Ala Gly His
        20                  25                  30 tgt gga gga tca gga gct tca gct aca aca agt agt ggt gag gcc cta     702
Cys Gly Gly Ser Gly Ala Ser Ala Thr Thr Ser Ser Gly Glu Ala Leu
 35                  40                  45 gga acc ttt tcg ggc tcc gtc ttc cct ggc agt gcc gac atg gcc tac     750
Gly Thr Phe Ser Gly Ser Val Phe Pro Gly Ser Ala Asp Met Ala Tyr
     50                  55                  60 gtc cgc act gta agt gga aca gtc ctt aga ggc tac atc aac ggc tac     798
Val Arg Thr Val Ser Gly Thr Val Leu Arg Gly Tyr Ile Asn Gly Tyr
 65                  70                  75                  80 ggc caa ggg agc ttt ccc gtc tca gga agc tcc gag gct gcc gtt gga     846
Gly Gln Gly Ser Phe Pro Val Ser Gly Ser Ser Glu Ala Ala Val Gly
                 85                  90                  95 gct agc atc tgc cgc tcc ggc tca acc act caa gtc cac tgc ggc acg     894
Ala Ser Ile Cys Arg Ser Gly Ser Thr Thr Gln Val His Cys Gly Thr
             100                 105                 110 att ggt gcc aag ggc gcc acg gtt aac tac cct caa gga gct gtt tcg     942
Ile Gly Ala Lys Gly Ala Thr Val Asn Tyr Pro Gln Gly Ala Val Ser
         115                 120                 125 ggc ctc act cgg act agc gtc tgc gcc gag ccc ggc gac tca ggc ggt     990
Gly Leu Thr Arg Thr Ser Val Cys Ala Glu Pro Gly Asp Ser Gly Gly
     130                 135                 140 tct ttc tac tcc ggc tcc cag gcg cag ggt gtc acc tcg gga ggc agc    1038
Ser Phe Tyr Ser Gly Ser Gln Ala Gln Gly Val Thr Ser Gly Gly Ser
145                 150                 155                 160 ggc gac tgc agc cgt gga ggc acg acc tat ttc cag cct gtt aat agg    1086
Gly Asp Cys Ser Arg Gly Gly Thr Thr Tyr Phe Gln Pro Val Asn Arg
                165                 170                 175 atc ctc cag aca tat ggc ctt acc ttg gtc acg gcg tag                1125
Ile Leu Gln Thr Tyr Gly Leu Thr Leu Val Thr Ala
            180                 185

<210> SEQ ID NO 4
<211> LENGTH: 374
<212> TYPE: PRT
<213> ORGANISM: Metarhizium anisopliae

<400> SEQUENCE: 4

Met Glu  Leu Thr Lys Phe  Leu Ala Leu Leu  Ala Val  Ile Leu Pro
         -185                -180                 -175

Val Ala  Tyr Gly Ala Pro  Thr Gln Ala Ala  Ser Leu  His Pro Gln
    -170                -165                 -160

Ile Leu  Glu Ala Met Lys  Arg Asp Leu Gly  Leu Asn  Ala Glu Gln
    -155                -150                 -145

Ala Thr  Val Arg Val Ala  Arg Glu Ile His  Ala Thr  Asp Val Ile
    -140                -135                 -130

Glu Gln  Leu Arg Ser Ser  Val Ala Phe Ala  Gly Ala  Trp Ile Asp
    -125                -120                 -115

Ala Asp  Val Leu Tyr Ile  Gly Ile Thr Asp  Gln Ala  Leu Ala Asp
    -110                -105                 -100

Glu Val  Thr Ala Ala Gly  Ala Thr Pro Ile  Val Met  Thr Asn Ser Leu
     -95                 -90                  -85

Ser Lys  Leu Glu Lys Ala  Lys Glu Asp Leu  Asp Lys  Ile Phe Ile Gly
 -80                 -75                  -70                  -65

Arg Ala  Asn Thr Leu Glu  Thr Ser Ser Asp  Thr Ser  Ser Gly Ile Ala
             -60                 -55                  -50
```

-continued

```
Ser Tyr Phe Val Asp Val Ala Ala Asn Lys Leu Val Ile Glu Ala Leu
        -45              -40                 -35

Ala Asp Ser His Gly His Ala Glu Gln Leu Ala Ala Gln Val Gly Leu
    -30              -25                  -20

Thr Ser Glu Phe Glu Val Arg Thr Val Glu Thr Met Pro Thr Thr Met
    -15              -10                   -5                -1

Ala Thr Val Gln Gly Gly Asp Val Tyr Tyr Ile Asn Arg Ser Ser Arg
1                 5                  10                  15

Cys Ser Ile Gly Phe Ala Val Thr Thr Gly Phe Val Ser Ala Gly His
                20                  25                  30

Cys Gly Gly Ser Gly Ala Ser Ala Thr Thr Ser Ser Gly Glu Ala Leu
                35                  40                  45

Gly Thr Phe Ser Gly Ser Val Phe Pro Gly Ser Ala Asp Met Ala Tyr
    50                  55                  60

Val Arg Thr Val Ser Gly Thr Val Leu Arg Gly Tyr Ile Asn Gly Tyr
65                  70                  75                  80

Gly Gln Gly Ser Phe Pro Val Ser Gly Ser Ser Glu Ala Ala Val Gly
                85                  90                  95

Ala Ser Ile Cys Arg Ser Gly Ser Thr Thr Gln Val His Cys Gly Thr
                100                 105                 110

Ile Gly Ala Lys Gly Ala Thr Val Asn Tyr Pro Gln Gly Ala Val Ser
                115                 120                 125

Gly Leu Thr Arg Thr Ser Val Cys Ala Glu Pro Gly Asp Ser Gly Gly
                130                 135                 140

Ser Phe Tyr Ser Gly Ser Gln Ala Gln Gly Val Thr Ser Gly Gly Ser
145                 150                 155                 160

Gly Asp Cys Ser Arg Gly Gly Thr Thr Tyr Phe Gln Pro Val Asn Arg
                165                 170                 175

Ile Leu Gln Thr Tyr Gly Leu Thr Leu Val Thr Ala
                180                 185
```

<210> SEQ ID NO 5
<211> LENGTH: 1062
<212> TYPE: DNA
<213> ORGANISM: Nocardiopsis prasina DSM 15648
<220> FEATURE:
<221> NAME/KEY: CDS
<222> LOCATION: (1)..(1059)
<220> FEATURE:
<221> NAME/KEY: mat_peptide
<222> LOCATION: (496)..(1059)

<400> SEQUENCE: 5

```
gcc acc gga ccg ctc ccc cag tca ccc acc ccg gag gcc gac gcc         45
Ala Thr Gly Pro Leu Pro Gln Ser Pro Thr Pro Glu Ala Asp Ala
-165                -160                -155 gtc tcc atg cag gag gcg ctc cag cgc gac ctc ggc ctg acc ccg         90
Val Ser Met Gln Glu Ala Leu Gln Arg Asp Leu Gly Leu Thr Pro
-150                -145                -140 ctt gag gcc gat gaa ctg ctg gcc gcc cag gac acc gcc ttc gag        135
Leu Glu Ala Asp Glu Leu Leu Ala Ala Gln Asp Thr Ala Phe Glu
-135                -130                -125 gtc gac gag gcc gcg gcc gcg gcc gcc ggg gac gcc tac ggc ggc        180
Val Asp Glu Ala Ala Ala Ala Ala Ala Gly Asp Ala Tyr Gly Gly
-120                -115                -110 tcc gtc ttc gac acc gag acc ctg gaa ctg acc gtc ctg gtc acc gac   228
Ser Val Phe Asp Thr Glu Thr Leu Glu Leu Thr Val Leu Val Thr Asp
-105                -100                 -95                 -90
```

| | | |
|---|---|---|
| gcc gcc tcg gtc gag gct gtg gag gcc acc ggc gcg ggt acc gaa ctc<br>Ala Ala Ser Val Glu Ala Val Glu Ala Thr Gly Ala Gly Thr Glu Leu<br>            -85                        -80                           -75 | | 276 |
| gtc tcc tac ggc atc gag ggc ctc gac gag atc atc cag gat ctc aac<br>Val Ser Tyr Gly Ile Glu Gly Leu Asp Glu Ile Ile Gln Asp Leu Asn<br>           -70                         -65                          -60 | | 324 |
| gcc gcc gac gcc gtc ccc ggc gtg gtc ggc tgg tac ccg gac gtg gcg<br>Ala Ala Asp Ala Val Pro Gly Val Val Gly Trp Tyr Pro Asp Val Ala<br>        -55                       -50                      -45 | | 372 |
| ggt gac acc gtc gtc ctg gag gtc ctg gag ggt tcc gga gcc gac gtg<br>Gly Asp Thr Val Val Leu Glu Val Leu Glu Gly Ser Gly Ala Asp Val<br>-40                       -35                     -30 | | 420 |
| agc ggc ctg ctc gcc gac gcc ggc gtg gac gcc tcg gcc gtc gag gtg<br>Ser Gly Leu Leu Ala Asp Ala Gly Val Asp Ala Ser Ala Val Glu Val<br>-25                 -20                     -15                     -10 | | 468 |
| acc agc agt gcg cag ccc gag ctc tac gcc gac atc atc ggc ggt ctg<br>Thr Ser Ser Ala Gln Pro Glu Leu Tyr Ala Asp Ile Ile Gly Gly Leu<br>            -5                   -1  1                          5 | | 516 |
| gcc tac acc atg ggc ggc cgc tgt tcg gtc gga ttc gcg gcc acc aac<br>Ala Tyr Thr Met Gly Gly Arg Cys Ser Val Gly Phe Ala Ala Thr Asn<br>          10                         15                      20 | | 564 |
| gcc gcc ggt cag ccc gga ttc gtc acc gcc ggt cac tgt ggc cgc gtg<br>Ala Ala Gly Gln Pro Gly Phe Val Thr Ala Gly His Cys Gly Arg Val<br>25                      30                      35 | | 612 |
| ggc acc cag gtg agc atc ggc aac ggc cag ggc gtc ttc gag cag tcc<br>Gly Thr Gln Val Ser Ile Gly Asn Gly Gln Gly Val Phe Glu Gln Ser<br>40                  45                      50                    55 | | 660 |
| atc ttc ccg ggc aac gac gcc gcc ttc gtc cgc ggc acg tcc aac ttc<br>Ile Phe Pro Gly Asn Asp Ala Ala Phe Val Arg Gly Thr Ser Asn Phe<br>              60                        65                      70 | | 708 |
| acg ctg acc aac ctg gtc agc cgc tac aac acc ggc ggt tac gcc acc<br>Thr Leu Thr Asn Leu Val Ser Arg Tyr Asn Thr Gly Gly Tyr Ala Thr<br>          75                         80                       85 | | 756 |
| gtc gcc ggc cac aac cag gcg ccc atc ggc tcc tcc gtc tgc cgc tcc<br>Val Ala Gly His Asn Gln Ala Pro Ile Gly Ser Ser Val Cys Arg Ser<br>            90                        95                      100 | | 804 |
| ggc tcc acc acc ggc tgg cac tgc ggc acc atc cag gcc cgc ggc cag<br>Gly Ser Thr Thr Gly Trp His Cys Gly Thr Ile Gln Ala Arg Gly Gln<br>        105                     110                     115 | | 852 |
| tcg gtg agc tac ccc gag ggc acc gtc acc aac atg acc cgg acc acc<br>Ser Val Ser Tyr Pro Glu Gly Thr Val Thr Asn Met Thr Arg Thr Thr<br>120                   125                     130                   135 | | 900 |
| gtg tgc gcc gag ccc ggc gac tcc ggc ggc tcc tac atc tcc ggc aac<br>Val Cys Ala Glu Pro Gly Asp Ser Gly Gly Ser Tyr Ile Ser Gly Asn<br>              140                     145                     150 | | 948 |
| cag gcc cag ggc gtc acc tcc ggc ggc tcc ggc aac tgc cgc acc ggc<br>Gln Ala Gln Gly Val Thr Ser Gly Gly Ser Gly Asn Cys Arg Thr Gly<br>            155                    160                     165 | | 996 |
| ggg acc acc ttc tac cag gag gtc acc ccc atg gtg aac tcc tgg ggc<br>Gly Thr Thr Phe Tyr Gln Glu Val Thr Pro Met Val Asn Ser Trp Gly<br>        170                     175                     180 | | 1044 |
| gtc cgt ctc cgg acc taa<br>Val Arg Leu Arg Thr<br>        185 | | 1062 |

<210> SEQ ID NO 6
<211> LENGTH: 353
<212> TYPE: PRT
<213> ORGANISM: Nocardiopsis prasina DSM 15648

<400> SEQUENCE: 6

```
Ala Thr Gly Pro Leu Pro Gln Ser Pro Thr Pro Glu Ala Asp Ala
-165                 -160                 -155

Val Ser Met Gln Glu Ala Leu Gln Arg Asp Leu Gly Leu Thr Pro
-150                 -145                 -140

Leu Glu Ala Asp Glu Leu Leu Ala Ala Gln Asp Thr Ala Phe Glu
-135                 -130                 -125

Val Asp Glu Ala Ala Ala Ala Ala Ala Gly Asp Ala Tyr Gly Gly
-120                 -115                 -110

Ser Val Phe Asp Thr Glu Thr Leu Glu Leu Thr Val Leu Val Thr Asp
-105                 -100                  -95                  -90

Ala Ala Ser Val Glu Ala Val Glu Ala Thr Gly Ala Gly Thr Glu Leu
                 -85                  -80                  -75

Val Ser Tyr Gly Ile Glu Gly Leu Asp Glu Ile Ile Gln Asp Leu Asn
             -70                  -65                  -60

Ala Ala Asp Ala Val Pro Gly Val Val Gly Trp Tyr Pro Asp Val Ala
         -55                  -50                  -45

Gly Asp Thr Val Val Leu Glu Val Leu Glu Gly Ser Gly Ala Asp Val
     -40                  -35                  -30

Ser Gly Leu Leu Ala Asp Ala Gly Val Asp Ala Ser Ala Val Glu Val
-25                  -20                  -15                  -10

Thr Ser Ser Ala Gln Pro Glu Leu Tyr Ala Asp Ile Ile Gly Gly Leu
             -5                   -1   1                    5

Ala Tyr Thr Met Gly Gly Arg Cys Ser Val Gly Phe Ala Ala Thr Asn
             10                  15                   20

Ala Ala Gly Gln Pro Gly Phe Val Thr Ala Gly His Cys Gly Arg Val
         25                  30                   35

Gly Thr Gln Val Ser Ile Gly Asn Gly Gln Gly Val Phe Glu Gln Ser
40                   45                  50                   55

Ile Phe Pro Gly Asn Asp Ala Ala Phe Val Arg Gly Thr Ser Asn Phe
                 60                  65                   70

Thr Leu Thr Asn Leu Val Ser Arg Tyr Asn Thr Gly Gly Tyr Ala Thr
             75                  80                   85

Val Ala Gly His Asn Gln Ala Pro Ile Gly Ser Ser Val Cys Arg Ser
         90                  95                  100

Gly Ser Thr Thr Gly Trp His Cys Gly Thr Ile Gln Ala Arg Gly Gln
    105                 110                  115

Ser Val Ser Tyr Pro Glu Gly Thr Val Thr Asn Met Thr Arg Thr Thr
120                 125                  130                  135

Val Cys Ala Glu Pro Gly Asp Ser Gly Gly Ser Tyr Ile Ser Gly Asn
        140                  145                 150

Gln Ala Gln Gly Val Thr Ser Gly Gly Ser Gly Asn Cys Arg Thr Gly
            155                  160                 165

Gly Thr Thr Phe Tyr Gln Glu Val Thr Pro Met Val Asn Ser Trp Gly
        170                  175                 180

Val Arg Leu Arg Thr
    185

<210> SEQ ID NO 7
<211> LENGTH: 1062
<212> TYPE: DNA
<213> ORGANISM: Nocardiopsis prasina DSM 15649
<220> FEATURE:
<221> NAME/KEY: CDS
<222> LOCATION: (1)..(1059)
<220> FEATURE:
```

```
<221> NAME/KEY: mat_peptide
<222> LOCATION: (496)..(1059)

<400> SEQUENCE: 7 gcc acc gga cca ctc ccc cag tca ccc acc ccg gag gcc gac gcc      45
Ala Thr Gly Pro Leu Pro Gln Ser Pro Thr Pro Glu Ala Asp Ala
-165            -160                -155 gtc tcc atg cag gag gcg ctc cag cgc gac ctc ggc ctg acc ccg      90
Val Ser Met Gln Glu Ala Leu Gln Arg Asp Leu Gly Leu Thr Pro
-150            -145                -140 ctt gag gcc gat gaa ctg ctg gcc gcc cag gac acc gcc ttc gag     135
Leu Glu Ala Asp Glu Leu Leu Ala Ala Gln Asp Thr Ala Phe Glu
-135            -130                -125 gtc gac gag gcc gcg gcc gag gcc gcc ggt gac gcc tac ggc ggc     180
Val Asp Glu Ala Ala Ala Glu Ala Ala Gly Asp Ala Tyr Gly Gly
-120            -115                -110 tcc gtc ttc gac acc gag acc ctg gaa ctg acc gtc ctg gtc acc gac   228
Ser Val Phe Asp Thr Glu Thr Leu Glu Leu Thr Val Leu Val Thr Asp
-105            -100                -95                 -90 tcc gcc gcg gtc gag gcg gtg gag gcc acc ggc gcc ggg acc gaa ctg   276
Ser Ala Ala Val Glu Ala Val Glu Ala Thr Gly Ala Gly Thr Glu Leu
                -85                 -80                 -75 gtc tcc tac ggc atc acg ggc ctc gac gag atc gtc gag gag ctc aac   324
Val Ser Tyr Gly Ile Thr Gly Leu Asp Glu Ile Val Glu Glu Leu Asn
            -70                 -65                 -60 gcc gcc gac gcc gtt ccc ggc gtg gtc ggc tgg tac ccg gac gtc gcg   372
Ala Ala Asp Ala Val Pro Gly Val Val Gly Trp Tyr Pro Asp Val Ala
            -55                 -50                 -45 ggt gac acc gtc gtg ctg gag gtc ctg gag ggt tcc ggc gcc gac gtg   420
Gly Asp Thr Val Val Leu Glu Val Leu Glu Gly Ser Gly Ala Asp Val
            -40                 -35                 -30 ggc ggc ctg ctc gcc gac gcc ggc gtg gac gcc tcg gcg gtc gag gtg   468
Gly Gly Leu Leu Ala Asp Ala Gly Val Asp Ala Ser Ala Val Glu Val
-25             -20                 -15                 -10 acc acc acc gag cag ccc gag ctg tac gcc gac atc atc ggc ggt ctg   516
Thr Thr Thr Glu Gln Pro Glu Leu Tyr Ala Asp Ile Ile Gly Gly Leu
            -5                  -1  1                   5 gcc tac acc atg ggc ggc cgc tgt tcg gtc ggc ttc gcg gcc acc aac   564
Ala Tyr Thr Met Gly Gly Arg Cys Ser Val Gly Phe Ala Ala Thr Asn
            10                  15                  20 gcc gcc ggt cag ccc ggg ttc gtc acc gcc ggt cac tgt ggc cgc gtg   612
Ala Ala Gly Gln Pro Gly Phe Val Thr Ala Gly His Cys Gly Arg Val
25              30                  35 ggc acc cag gtg acc atc ggc aac ggc cgg ggc gtc ttc gag cag tcc   660
Gly Thr Gln Val Thr Ile Gly Asn Gly Arg Gly Val Phe Glu Gln Ser
40              45                  50                  55 atc ttc ccg ggc aac gac gcc gcc ttc gtc cgc gga acg tcc aac ttc   708
Ile Phe Pro Gly Asn Asp Ala Ala Phe Val Arg Gly Thr Ser Asn Phe
                60                  65                  70 acg ctg acc aac ctg gtc agc cgc tac aac acc ggc ggc tac gcc acc   756
Thr Leu Thr Asn Leu Val Ser Arg Tyr Asn Thr Gly Gly Tyr Ala Thr
            75                  80                  85 gtc gcc ggt cac aac cag gcg ccc atc ggc tcc tcc gtc tgc cgc tcc   804
Val Ala Gly His Asn Gln Ala Pro Ile Gly Ser Ser Val Cys Arg Ser
            90                  95                  100 ggc tcc acc acc ggt tgg cac tgc ggc acc atc cag gcc cgc ggc cag   852
Gly Ser Thr Thr Gly Trp His Cys Gly Thr Ile Gln Ala Arg Gly Gln
105             110                 115 tcg gtg agc tac ccc gag ggc acc gtc acc aac atg acg cgg acc acc   900
Ser Val Ser Tyr Pro Glu Gly Thr Val Thr Asn Met Thr Arg Thr Thr
```

```
                    120                125                130                135
gtg tgc gcc gag ccc ggc gac tcc ggc ggc tcc tac atc tcc ggc aac        948
Val Cys Ala Glu Pro Gly Asp Ser Gly Gly Ser Tyr Ile Ser Gly Asn
                    140                145                150 cag gcc cag ggc gtc acc tcc ggc ggc tcc ggc aac tgc cgc acc ggc        996
Gln Ala Gln Gly Val Thr Ser Gly Gly Ser Gly Asn Cys Arg Thr Gly
                155                160                165 ggg acc acc ttc tac cag gag gtc acc ccc atg gtg aac tcc tgg ggc       1044
Gly Thr Thr Phe Tyr Gln Glu Val Thr Pro Met Val Asn Ser Trp Gly
            170                175                180 gtc cgt ctc cgg acc taa                                                1062
Val Arg Leu Arg Thr
        185

<210> SEQ ID NO 8
<211> LENGTH: 353
<212> TYPE: PRT
<213> ORGANISM: Nocardiopsis prasina DSM 15649

<400> SEQUENCE: 8

Ala  Thr Gly Pro Leu Pro  Gln Ser Pro Thr  Pro  Glu Ala Asp Ala
-165              -160               -155

Val  Ser Met Gln Glu Ala  Leu Gln Arg Asp Leu  Gly Leu Thr Pro
-150              -145                -140

Leu  Glu Ala Asp Glu Leu  Leu Ala Ala Gln Asp  Thr Ala Phe Glu
-135              -130                -125

Val  Asp Glu Ala Ala Ala  Glu Ala Ala Gly Asp  Ala Tyr Gly Gly
-120              -115                -110

Ser  Val Phe Asp Thr Glu  Thr Leu Glu Leu Thr Val Leu Val Thr Asp
-105              -100                -95                       -90

Ser Ala Ala Val Glu Ala Val Glu Ala Thr Gly Ala Gly Thr Glu Leu
            -85                -80                -75

Val Ser Tyr Gly Ile Thr Gly Leu Asp Glu Ile Val Glu Glu Leu Asn
        -70                -65                -60

Ala Ala Asp Ala Val Pro Gly Val Val Gly Trp Tyr Pro Asp Val Ala
        -55                -50                -45

Gly Asp Thr Val Val Leu Glu Val Leu Glu Gly Ser Gly Ala Asp Val
        -40                -35                -30

Gly Gly Leu Leu Ala Asp Ala Gly Val Asp Ala Ser Ala Val Glu Val
    -25                -20                -15                -10

Thr Thr Thr Glu Gln Pro Glu Leu Tyr Ala Asp Ile Ile Gly Gly Leu
                -5                 -1  1                 5

Ala Tyr Thr Met Gly Gly Arg Cys Ser Val Gly Phe Ala Ala Thr Asn
            10                 15                20

Ala Ala Gly Gln Pro Gly Phe Val Thr Ala Gly His Cys Gly Arg Val
        25                 30                 35

Gly Thr Gln Val Thr Ile Gly Asn Gly Arg Gly Val Phe Glu Gln Ser
40                 45                 50                 55

Ile Phe Pro Gly Asn Asp Ala Ala Phe Val Arg Gly Thr Ser Asn Phe
            60                 65                 70

Thr Leu Thr Asn Leu Val Ser Arg Tyr Asn Thr Gly Gly Tyr Ala Thr
            75                 80                 85

Val Ala Gly His Asn Gln Ala Pro Ile Gly Ser Ser Val Cys Arg Ser
        90                 95                 100

Gly Ser Thr Thr Gly Trp His Cys Gly Thr Ile Gln Ala Arg Gly Gln
    105                110                115
```

```
Ser Val Ser Tyr Pro Glu Gly Thr Val Thr Asn Met Thr Arg Thr Thr
120                 125                 130                 135

Val Cys Ala Glu Pro Gly Asp Ser Gly Gly Ser Tyr Ile Ser Gly Asn
            140                 145                 150

Gln Ala Gln Gly Val Thr Ser Gly Gly Ser Gly Asn Cys Arg Thr Gly
        155                 160                 165

Gly Thr Thr Phe Tyr Gln Glu Val Thr Pro Met Val Asn Ser Trp Gly
    170                 175                 180

Val Arg Leu Arg Thr
        185

<210> SEQ ID NO 9
<211> LENGTH: 1068
<212> TYPE: DNA
<213> ORGANISM: Nocardiopsis alba
<220> FEATURE:
<221> NAME/KEY: CDS
<222> LOCATION: (1)..(1065)
<220> FEATURE:
<221> NAME/KEY: mat_peptide
<222> LOCATION: (502)..(1065)

<400> SEQUENCE: 9 gcg acc ggc ccc ctc ccc cag tcc ccc acc ccg gat gaa gcc gag          45
Ala Thr Gly Pro Leu Pro Gln Ser Pro Thr Pro Asp Glu Ala Glu
        -165                -160                -155 gcc acc acc atg gtc gag gcc ctc cag cgc gac ctc ggc ctg tcc          90
Ala Thr Thr Met Val Glu Ala Leu Gln Arg Asp Leu Gly Leu Ser
        -150                -145                -140 ccc tct cag gcc gac gag ctc ctc gag gcg cag gcc gag tcc ttc         135
Pro Ser Gln Ala Asp Glu Leu Leu Glu Ala Gln Ala Glu Ser Phe
        -135                -130                -125 gag atc gac gag gcc gcc acc gcg gcc gca gcc gac tcc tac ggc         180
Glu Ile Asp Glu Ala Ala Thr Ala Ala Ala Ala Asp Ser Tyr Gly
        -120                -115                -110 ggc tcc atc ttc gac acc gac agc ctc acc ctg acc gtc ctg gtc acc     228
Gly Ser Ile Phe Asp Thr Asp Ser Leu Thr Leu Thr Val Leu Val Thr
        -105                -100                -95 gac gcc tcc gcc gtc gag gcg gtc gag gcc gcc ggc gcc gag gcc aag     276
Asp Ala Ser Ala Val Glu Ala Val Glu Ala Ala Gly Ala Glu Ala Lys
    -90                 -85                 -80 gtg gtc tcg cac ggc atg gag ggc ctg gag gag atc gtc gcc gac ctg     324
Val Val Ser His Gly Met Glu Gly Leu Glu Glu Ile Val Ala Asp Leu
-75                 -70                 -65                 -60 aac gcg gcc gac gct cag ccc ggc gtc gtg ggc tgg tac ccc gac atc     372
Asn Ala Ala Asp Ala Gln Pro Gly Val Val Gly Trp Tyr Pro Asp Ile
            -55                 -50                 -45 cac tcc gac acg gtc gtc ctc gag gtc ctc gag ggc tcc ggt gcc gac     420
His Ser Asp Thr Val Val Leu Glu Val Leu Glu Gly Ser Gly Ala Asp
        -40                 -35                 -30 gtg gac tcc ctg ctc gcc gac gcc ggt gtg gac acc gcc gac gtc aag     468
Val Asp Ser Leu Leu Ala Asp Ala Gly Val Asp Thr Ala Asp Val Lys
    -25                 -20                 -15 gtg gag agc acc acc gag cag ccc gag ctg tac gcc gac atc atc ggc     516
Val Glu Ser Thr Thr Glu Gln Pro Glu Leu Tyr Ala Asp Ile Ile Gly
-10                 -5                  -1  1                5 ggt ctc gcc tac acc atg ggt ggg cgc tgc tcg gtc ggc ttc gcg gcc     564
Gly Leu Ala Tyr Thr Met Gly Gly Arg Cys Ser Val Gly Phe Ala Ala
                10                  15                  20 acc aac gcc tcc ggc cag ccc ggg ttc gtc acc gcc ggc cac tgc ggc     612
```

-continued

```
                Thr Asn Ala Ser Gly Gln Pro Gly Phe Val Thr Ala Gly His Cys Gly
                             25                  30                  35 acc gtc ggc acc ccg gtc agc atc ggc aac ggc cag ggc gtc ttc gag        660
Thr Val Gly Thr Pro Val Ser Ile Gly Asn Gly Gln Gly Val Phe Glu
         40                  45                  50 cgt tcc gtc ttc ccc ggc aac gac tcc gcc ttc gtc cgc ggc acc tcg        708
Arg Ser Val Phe Pro Gly Asn Asp Ser Ala Phe Val Arg Gly Thr Ser
 55                  60                  65 aac ttc acc ctg acc aac ctg gtc agc cgc tac aac acc ggt ggt tac        756
Asn Phe Thr Leu Thr Asn Leu Val Ser Arg Tyr Asn Thr Gly Gly Tyr
 70                  75                  80                  85 gcg acc gtc tcc ggc tcc tcg cag gcg gcg atc ggc tcg cag atc tgc        804
Ala Thr Val Ser Gly Ser Ser Gln Ala Ala Ile Gly Ser Gln Ile Cys
                 90                  95                 100 cgt tcc ggc tcc acc acc ggc tgg cac tgc ggc acc gtc cag gcc cgc        852
Arg Ser Gly Ser Thr Thr Gly Trp His Cys Gly Thr Val Gln Ala Arg
             105                 110                 115 ggc cag acg gtg agc tac ccc cag ggc acc gtg cag aac ctg acc cgc        900
Gly Gln Thr Val Ser Tyr Pro Gln Gly Thr Val Gln Asn Leu Thr Arg
         120                 125                 130 acc aac gtc tgc gcc gag ccc ggt gac tcc ggc tcc ttc atc tcc            948
Thr Asn Val Cys Ala Glu Pro Gly Asp Ser Gly Ser Phe Ile Ser
 135                 140                 145 ggc agc cag gcc cag ggc gtc acc tcc ggt ggc tcc ggc aac tgc tcc        996
Gly Ser Gln Ala Gln Gly Val Thr Ser Gly Gly Ser Gly Asn Cys Ser
150                 155                 160                 165 ttc ggt ggc acc acc tac tac cag gag gtc aac ccg atg ctg agc agc       1044
Phe Gly Gly Thr Thr Tyr Tyr Gln Glu Val Asn Pro Met Leu Ser Ser
                 170                 175                 180 tgg ggt ctg acc ctg cgc acc tga                                       1068
Trp Gly Leu Thr Leu Arg Thr
             185

<210> SEQ ID NO 10
<211> LENGTH: 355
<212> TYPE: PRT
<213> ORGANISM: Nocardiopsis alba

<400> SEQUENCE: 10

Ala Thr Gly Pro Leu Pro Gln Ser Pro Thr Pro Asp Glu Ala Glu
         -165                -160                -155

Ala Thr Thr Met Val Glu Ala Leu Gln Arg Asp Leu Gly Leu Ser
         -150                -145                -140

Pro Ser Gln Ala Asp Glu Leu Leu Glu Ala Gln Ala Glu Ser Phe
         -135                -130                -125

Glu Ile Asp Glu Ala Ala Thr Ala Ala Ala Ala Asp Ser Tyr Gly
         -120                -115                -110

Gly Ser Ile Phe Asp Thr Asp Ser Leu Thr Leu Thr Val Leu Thr
         -105                -100                 -95

Asp Ala Ser Ala Val Glu Ala Val Glu Ala Gly Ala Glu Ala Lys
          -90                 -85                 -80

Val Val Ser His Gly Met Glu Gly Leu Glu Glu Ile Val Ala Asp Leu
 -75                 -70                 -65                 -60

Asn Ala Ala Asp Ala Gln Pro Gly Val Val Gly Trp Tyr Pro Asp Ile
                 -55                 -50                 -45

His Ser Asp Thr Val Val Leu Glu Val Leu Glu Gly Ser Gly Ala Asp
          -40                 -35                 -30

Val Asp Ser Leu Leu Ala Asp Ala Gly Val Asp Thr Ala Asp Val Lys
```

```
                -25                 -20                 -15
Val Glu Ser Thr Thr Glu Gln Pro Glu Leu Tyr Ala Asp Ile Ile Gly
        -10                 -5              -1   1                   5

Gly Leu Ala Tyr Thr Met Gly Gly Arg Cys Ser Val Gly Phe Ala Ala
                     10                  15                  20

Thr Asn Ala Ser Gly Gln Pro Gly Phe Val Thr Ala Gly His Cys Gly
             25                  30                  35

Thr Val Gly Thr Pro Val Ser Ile Gly Asn Gly Gln Gly Val Phe Glu
         40                  45                  50

Arg Ser Val Phe Pro Gly Asn Asp Ser Ala Phe Val Arg Gly Thr Ser
     55                  60                  65

Asn Phe Thr Leu Thr Asn Leu Val Ser Arg Tyr Asn Thr Gly Gly Tyr
70              75                  80                      85

Ala Thr Val Ser Gly Ser Ser Gln Ala Ala Ile Gly Ser Gln Ile Cys
                 90                  95                 100

Arg Ser Gly Ser Thr Thr Gly Trp His Cys Gly Thr Val Gln Ala Arg
             105                 110                 115

Gly Gln Thr Val Ser Tyr Pro Gln Gly Thr Val Gln Asn Leu Thr Arg
             120                 125                 130

Thr Asn Val Cys Ala Glu Pro Gly Asp Ser Gly Gly Ser Phe Ile Ser
         135                 140                 145

Gly Ser Gln Ala Gln Gly Val Thr Ser Gly Gly Ser Gly Asn Cys Ser
150                 155                 160                 165

Phe Gly Gly Thr Thr Tyr Tyr Gln Glu Val Asn Pro Met Leu Ser Ser
                     170                 175                 180

Trp Gly Leu Thr Leu Arg Thr
                 185

<210> SEQ ID NO 11
<211> LENGTH: 1065
<212> TYPE: DNA
<213> ORGANISM: Nocardiopsis dassonvillei subspecies dassonvillei
<220> FEATURE:
<221> NAME/KEY: CDS
<222> LOCATION: (1)..(1062)
<220> FEATURE:
<221> NAME/KEY: mat_peptide
<222> LOCATION: (499)..(1062)

<400> SEQUENCE: 11 gct ccg gcc ccc gtc ccc cag  acc ccc gtc gcc gac  gac agc gcc        45
Ala Pro Ala Pro Val Pro Gln  Thr Pro Val Ala Asp  Asp Ser Ala
    -165                -160                 -155 gcc agc atg acc gag gcg ctc  aag cgc gac ctc gac  ctc acc tcg        90
Ala Ser Met Thr Glu Ala Leu  Lys Arg Asp Leu Asp  Leu Thr Ser
    -150                -145                 -140 gcc gag gcc gag gag ctt ctc  tcg gcg cag gaa gcc  gcc atc gag       135
Ala Glu Ala Glu Glu Leu Leu  Ser Ala Gln Glu Ala  Ala Ile Glu
    -135                -130                 -125 acc gac gcc gag gcc acc gag  gcc gcg ggc gag gcc  tac ggc ggc       180
Thr Asp Ala Glu Ala Thr Glu  Ala Ala Gly Glu Ala  Tyr Gly Gly
    -120                -115                 -110 tca ctg ttc gac acc gag acc  ctc gaa ctc acc gtg ctg gtc acc gac   228
Ser Leu Phe Asp Thr Glu Thr  Leu Glu Leu Thr Val Leu Val Thr Asp
    -105                -100                  -95 gcc tcc gcc gtc gag gcg gtc gag gcc acc gga gcc cag gcc acc gtc   276
Ala Ser Ala Val Glu Ala Val Glu Ala Thr Gly Ala Gln Ala Thr Val
-90                  -85                  -80                  -75
```

| | | | | | | | | | | | | | | | |
|---|---|---|---|---|---|---|---|---|---|---|---|---|---|---|---|
| gtc | tcc | cac | ggc | acc | gag | ggc | ctg | acc | gag | gtc | gtg | gag | gac | ctc | aac | 324 |
| Val | Ser | His | Gly | Thr | Glu | Gly | Leu | Thr | Glu | Val | Val | Glu | Asp | Leu | Asn | |
| | | | -70 | | | | -65 | | | | -60 | | | | | |

(324)

ggc gcc gag gtt ccc gag agc gtc ctc ggc tgg tac ccg gac gtg gag   372
Gly Ala Glu Val Pro Glu Ser Val Leu Gly Trp Tyr Pro Asp Val Glu
        -55             -50             -45 agc gac acc gtc gtg gtc gag gtg ctg gag ggc tcc gac gcc gac gtc   420
Ser Asp Thr Val Val Val Glu Val Leu Glu Gly Ser Asp Ala Asp Val
        -40             -35             -30 gcc gcc ctg ctc gcc gac gcc ggt gtg gac tcc tcg gtc cgg gtg        468
Ala Ala Leu Leu Ala Asp Ala Gly Val Asp Ser Ser Val Arg Val
    -25             -20             -15 gag gag gcc gag gag gcc ccg cag gtc tac gcc gac atc atc ggc ggc   516
Glu Glu Ala Glu Glu Ala Pro Gln Val Tyr Ala Asp Ile Ile Gly Gly
-10             -5             -1  1              5 ctg gcc tac tac atg ggc ggc cgc tgc tcc gtc ggc ttc gcc gcg acc   564
Leu Ala Tyr Tyr Met Gly Gly Arg Cys Ser Val Gly Phe Ala Ala Thr
            10              15              20 aac agc gcc ggt cag ccc ggt ttc gtc acc gcc ggc cac tgc ggc acc   612
Asn Ser Ala Gly Gln Pro Gly Phe Val Thr Ala Gly His Cys Gly Thr
        25              30              35 gtc ggc acc ggc gtg acc atc ggc aac ggc acc ggc acc ttc cag aac   660
Val Gly Thr Gly Val Thr Ile Gly Asn Gly Thr Gly Thr Phe Gln Asn
    40              45              50 tcg gtc ttc ccc ggc aac gac gcc gcc ttc gtc cgc ggc acc tcc aac   708
Ser Val Phe Pro Gly Asn Asp Ala Ala Phe Val Arg Gly Thr Ser Asn
55              60              65              70 ttc acc ctg acc aac ctg gtc tcg cgc tac aac tcc ggc ggc tac cag   756
Phe Thr Leu Thr Asn Leu Val Ser Arg Tyr Asn Ser Gly Gly Tyr Gln
        75              80              85 tcg gtg acc ggt acc agc cag gcc ccg gcc ggc tcg gcc gtg tgc cgc   804
Ser Val Thr Gly Thr Ser Gln Ala Pro Ala Gly Ser Ala Val Cys Arg
        90              95              100 tcc ggc tcc acc acc ggc tgg cac tgc ggc acc atc cag gcc cgc aac   852
Ser Gly Ser Thr Thr Gly Trp His Cys Gly Thr Ile Gln Ala Arg Asn
        105             110             115 cag acc gtg cgc tac ccg cag ggc acc gtc tac tcg ctc acc cgc acc   900
Gln Thr Val Arg Tyr Pro Gln Gly Thr Val Tyr Ser Leu Thr Arg Thr
    120             125             130 aac gtg tgc gcc gag ccc ggc gac tcc ggc ggt tcg ttc atc tcc ggc   948
Asn Val Cys Ala Glu Pro Gly Asp Ser Gly Gly Ser Phe Ile Ser Gly
135             140             145             150 tcg cag gcc cag ggc gtc acc tcc ggc ggc tcc ggc aac tgc tcc gtc   996
Ser Gln Ala Gln Gly Val Thr Ser Gly Gly Ser Gly Asn Cys Ser Val
        155             160             165 ggc ggc acg acc tac tac cag gag gtc acc ccg atg atc aac tcc tgg   1044
Gly Gly Thr Thr Tyr Tyr Gln Glu Val Thr Pro Met Ile Asn Ser Trp
        170             175             180 ggt gtc agg atc cgg acc taa                                        1065
Gly Val Arg Ile Arg Thr
        185

<210> SEQ ID NO 12
<211> LENGTH: 354
<212> TYPE: PRT
<213> ORGANISM: Nocardiopsis dassonvillei subspecies dassonvillei

<400> SEQUENCE: 12

Ala Pro  Ala Pro Val Pro Gln  Thr Pro Val Ala Asp  Asp Ser Ala
    -165             -160             -155

```
Ala Ser Met Thr Glu Ala Leu Lys Arg Asp Leu Asp Leu Thr Ser
    -150             -145                 -140

Ala Glu Ala Glu Glu Leu Leu Ser Ala Gln Glu Ala Ala Ile Glu
    -135             -130                 -125

Thr Asp Ala Glu Ala Thr Glu Ala Ala Gly Glu Ala Tyr Gly Gly
    -120             -115                 -110

Ser Leu Phe Asp Thr Glu Thr Leu Glu Leu Thr Val Leu Val Thr Asp
    -105             -100                  -95

Ala Ser Ala Val Glu Ala Val Glu Ala Thr Gly Ala Gln Ala Thr Val
-90             -85              -80              -75

Val Ser His Gly Thr Glu Gly Leu Thr Glu Val Val Glu Asp Leu Asn
                -70              -65                  -60

Gly Ala Glu Val Pro Glu Ser Val Leu Gly Trp Tyr Pro Asp Val Glu
            -55              -50                  -45

Ser Asp Thr Val Val Val Glu Val Leu Glu Gly Ser Asp Ala Asp Val
        -40              -35                  -30

Ala Ala Leu Leu Ala Asp Ala Gly Val Asp Ser Ser Val Arg Val
    -25             -20                  -15

Glu Glu Ala Glu Glu Ala Pro Gln Val Tyr Ala Asp Ile Ile Gly Gly
-10             -5                   -1   1                5

Leu Ala Tyr Tyr Met Gly Gly Arg Cys Ser Val Gly Phe Ala Ala Thr
            10                  15                  20

Asn Ser Ala Gly Gln Pro Gly Phe Val Thr Ala Gly His Cys Gly Thr
            25                  30                  35

Val Gly Thr Gly Val Thr Ile Gly Asn Gly Thr Gly Thr Phe Gln Asn
        40                  45                  50

Ser Val Phe Pro Gly Asn Asp Ala Ala Phe Val Arg Gly Thr Ser Asn
55                  60                  65                  70

Phe Thr Leu Thr Asn Leu Val Ser Arg Tyr Asn Ser Gly Gly Tyr Gln
            75                  80                  85

Ser Val Thr Gly Thr Ser Gln Ala Pro Ala Gly Ser Ala Val Cys Arg
            90                  95                  100

Ser Gly Ser Thr Thr Gly Trp His Cys Gly Thr Ile Gln Ala Arg Asn
            105                 110                 115

Gln Thr Val Arg Tyr Pro Gln Gly Thr Val Tyr Ser Leu Thr Arg Thr
    120                 125                 130

Asn Val Cys Ala Glu Pro Gly Asp Ser Gly Gly Ser Phe Ile Ser Gly
135                 140                 145                 150

Ser Gln Ala Gln Gly Val Thr Ser Gly Gly Ser Gly Asn Cys Ser Val
            155                 160                 165

Gly Gly Thr Thr Tyr Tyr Gln Glu Val Thr Pro Met Ile Asn Ser Trp
            170                 175                 180

Gly Val Arg Ile Arg Thr
            185

<210> SEQ ID NO 13
<211> LENGTH: 1400
<212> TYPE: DNA
<213> ORGANISM: Brachysporiella gayana
<220> FEATURE:
<221> NAME/KEY: CDS
<222> LOCATION: (159)..(1283)
<220> FEATURE:
<221> NAME/KEY: mat_peptide
<222> LOCATION: (726)..(1283)

<400> SEQUENCE: 13
```

```
gtaggagctg tagaatcagc acatgaggca agtataaaag aaccagcatg ggatgatcaa      60
agtctgccaa ttcaaaggag caccatcaag ccgtcttgtc tagaactcct tgaacaccct     120
gtctactcca gtactcttgt cacagaacac atctagat atg gag ctc aca agc         173
                                          Met Glu Leu Thr Ser
                                                            -185 ctc atc gcc gca ctc gca gtt att ctg cct att gcc tac ggt gtt           218
Leu Ile Ala Ala Leu Ala Val Ile Leu Pro Ile Ala Tyr Gly Val
                -180             -175             -170 ccc atg gat gcc acc acc aac ctt tct ccc aag gtc ctg gcc gct           263
Pro Met Asp Ala Thr Thr Asn Leu Ser Pro Lys Val Leu Ala Ala
                -165             -160             -155 atg aag cgc gac ctg gga ctt gac gcc agg gag gcc act gcc cgt           308
Met Lys Arg Asp Leu Gly Leu Asp Ala Arg Glu Ala Thr Ala Arg
                -150             -145             -140 gtc acc ttc gaa cgt cgt gct ggc gat gtc atc gag gag ctg cgc           353
Val Thr Phe Glu Arg Arg Ala Gly Asp Val Ile Glu Glu Leu Arg
                -135             -130             -125 agc tcc ctg gga gat tcg ttc gcc ggt gct tgg gtt acg gat ggc           398
Ser Ser Leu Gly Asp Ser Phe Ala Gly Ala Trp Val Thr Asp Gly
                -120             -115             -110 aag gtc atc aac att ggt gtc act gat caa gct ttg gtc tcc aag gtt       446
Lys Val Ile Asn Ile Gly Val Thr Asp Gln Ala Leu Val Ser Lys Val
                -105             -100              -95 aag gaa gct ggc gct gaa ccg atg gtt atg aag aac agc ctc ggg aag       494
Lys Glu Ala Gly Ala Glu Pro Met Val Met Lys Asn Ser Leu Gly Lys
                 -90              -85              -80 ctt caa gag gca aag aag aag ctt gat cag atc atc aag gag aag ccg       542
Leu Gln Glu Ala Lys Lys Lys Leu Asp Gln Ile Ile Lys Glu Lys Pro
             -75              -70              -65 aag acc ctc agc acc tca ggc aag ccc ggc att gca aca tac tac gtt       590
Lys Thr Leu Ser Thr Ser Gly Lys Pro Gly Ile Ala Thr Tyr Tyr Val
             -60              -55              -50 gac att gag acc aac aag ctc atc atc acg gca ctc tcc acc agt atc       638
Asp Ile Glu Thr Asn Lys Leu Ile Ile Thr Ala Leu Ser Thr Ser Ile
-45              -40              -35              -30 act caa gct gaa gat ctg gct aag gag gtt ggc ctt tct gag tct gag       686
Thr Gln Ala Glu Asp Leu Ala Lys Glu Val Gly Leu Ser Glu Ser Glu
             -25              -20              -15 ttc gag gtg cgc aag act gag aag atg cca tcc cct ttc atc ctc ggc       734
Phe Glu Val Arg Lys Thr Glu Lys Met Pro Ser Pro Phe Ile Leu Gly
             -10              -5               -1   1 gga gac ccc ttt gtc atc aac aac agt gcc gtg tgc tct gtc ggc ttc       782
Gly Asp Pro Phe Val Ile Asn Asn Ser Ala Val Cys Ser Val Gly Phe
 5                10               15 gcc gtc tct ggc ggg ttt gtc tca gct ggc cac tgt ggc ggt caa ggc       830
Ala Val Ser Gly Gly Phe Val Ser Ala Gly His Cys Gly Gly Gln Gly
20               25               30               35 agc cct gtc acc tat atc gac ggt ggc gca ctt gga acg atc gaa gga       878
Ser Pro Val Thr Tyr Ile Asp Gly Gly Ala Leu Gly Thr Ile Glu Gly
                 40               45               50 tct gtc ttc ccc ggt gat gca gat atg tcc ttc atc cgt gcc gtt gac       926
Ser Val Phe Pro Gly Asp Ala Asp Met Ser Phe Ile Arg Ala Val Asp
             55               60               65 ggc act gac ctc cct ggc atc gtt ggt acc tat ggc aac ggt gat cag       974
Gly Thr Asp Leu Pro Gly Ile Val Gly Thr Tyr Gly Asn Gly Asp Gln
             70               75               80 ccc atc ttt ggc agc aat gtc gca ccc atc ggc tct ggt gtc tgc cgc      1022
Pro Ile Phe Gly Ser Asn Val Ala Pro Ile Gly Ser Gly Val Cys Arg
```

```
                    85                  90                  95
tca gga aca act acc ggc tat cac tgc ggc cag ctt gat gcc tac gac     1070
Ser Gly Thr Thr Thr Gly Tyr His Cys Gly Gln Leu Asp Ala Tyr Asp
100                 105                 110                 115 gtc act gtc aac tac gac gtg gga cct gtg ttc ggt ctt acc atg acc     1118
Val Thr Val Asn Tyr Asp Val Gly Pro Val Phe Gly Leu Thr Met Thr
                120                 125                 130 tct gct tgc gct gag cct gga gac tct ggc ggc tcc ttc ttt gcc ggt     1166
Ser Ala Cys Ala Glu Pro Gly Asp Ser Gly Gly Ser Phe Phe Ala Gly
            135                 140                 145 gac cag gct cag ggc gtc acc tcg gga ggt tct ggt gat tgc acc agc     1214
Asp Gln Ala Gln Gly Val Thr Ser Gly Gly Ser Gly Asp Cys Thr Ser
        150                 155                 160 ggt ggt cag acc ttc ttc cag ccc gtg aac gag att ctg gag acc tat     1262
Gly Gly Gln Thr Phe Phe Gln Pro Val Asn Glu Ile Leu Glu Thr Tyr
    165                 170                 175 ggt ctc tcg ctc acc acg gcc taattggatg aggctttgga cagccaagag        1313
Gly Leu Ser Leu Thr Thr Ala
180                 185 cctcaacttt tcatctgtat atagcaatta ttttcgtatc tcaagtactt agatcgtcac   1373
gatcaataca tatggacttc gcttggc                                       1400

<210> SEQ ID NO 14
<211> LENGTH: 375
<212> TYPE: PRT
<213> ORGANISM: Brachysporiella gayana

<400> SEQUENCE: 14

Met Glu Leu Thr Ser  Leu Ile Ala Ala  Leu Ala Val Ile Leu Pro
                -185            -180                 -175

Ile Ala Tyr Gly Val  Pro Met Asp Ala  Thr  Thr Asn Leu Ser Pro
                -170            -165                 -160

Lys Val Leu Ala Ala  Met Lys Arg Asp  Leu  Gly Leu Asp Ala Arg
                -155            -150                 -145

Glu Ala Thr Ala Arg  Val Thr Phe Glu Arg  Arg Ala Gly Asp Val
                -140            -135                 -130

Ile Glu Glu Leu Arg  Ser Ser Leu Gly Asp  Ser Phe Ala Gly Ala
                -125            -120                 -115

Trp Val Thr Asp Gly  Lys Val Ile Asn Ile  Gly Val Thr Asp Gln
                -110            -105                 -100

Ala Leu Val Ser Lys Val Lys Glu Ala Gly Ala Glu Pro Met Val Met
                -95                 -90                  -85

Lys Asn Ser Leu Gly Lys Leu Gln Glu Ala Lys Lys Lys Leu Asp Gln
            -80                 -75                  -70

Ile Ile Lys Glu Lys Pro Lys Thr Leu Ser Thr Ser Gly Lys Pro Gly
        -65                 -60                  -55

Ile Ala Thr Tyr Tyr Val Asp Ile Glu Thr Asn Lys Leu Ile Ile Thr
    -50                 -45                  -40

Ala Leu Ser Thr Ser Ile Thr Gln Ala Glu Asp Leu Ala Lys Glu Val
-35                 -30                  -25                  -20

Gly Leu Ser Glu Ser Glu Phe Glu Val Arg Lys Thr Glu Lys Met Pro
                -15                 -10                  -5

Ser Pro Phe Ile Leu Gly Gly Asp Pro Phe Val Ile Asn Asn Ser Ala
        -1  1                 5                   10

Val Cys Ser Val Gly Phe Ala Val Ser Gly Gly Phe Val Ser Ala Gly
    15                  20                  25
```

-continued

```
His Cys Gly Gly Gln Gly Ser Pro Val Thr Tyr Ile Asp Gly Gly Ala
 30              35                  40                  45

Leu Gly Thr Ile Glu Gly Ser Val Phe Pro Gly Asp Ala Asp Met Ser
             50                  55                  60

Phe Ile Arg Ala Val Asp Gly Thr Asp Leu Pro Gly Ile Val Gly Thr
             65                  70                  75

Tyr Gly Asn Gly Asp Gln Pro Ile Phe Gly Ser Asn Val Ala Pro Ile
         80                  85                  90

Gly Ser Gly Val Cys Arg Ser Gly Thr Thr Thr Gly Tyr His Cys Gly
     95                 100                 105

Gln Leu Asp Ala Tyr Asp Val Thr Val Asn Tyr Asp Val Gly Pro Val
110             115                 120                 125

Phe Gly Leu Thr Met Thr Ser Ala Cys Ala Glu Pro Gly Asp Ser Gly
             130                 135                 140

Gly Ser Phe Phe Ala Gly Asp Gln Ala Gln Gly Val Thr Ser Gly Gly
             145                 150                 155

Ser Gly Asp Cys Thr Ser Gly Gly Gln Thr Phe Phe Gln Pro Val Asn
            160                 165                 170

Glu Ile Leu Glu Thr Tyr Gly Leu Ser Leu Thr Thr Ala
            175             180             185
```

PROTEASES

CROSS-REFERENCE TO RELATED APPLICATIONS

This application is a 35 U.S.C. 371 national application of PCT/DK2004/000090 filed Feb. 9, 2004, which claims priority or the benefit under 35 U.S.C. 119 of Danish application nos. PA 2003 00173, PA 2003 00426, PA 2003 00912, PA 2003 00913, PA 2003 00914, PA 2003 00915, PA 2003 01492 and PA 2003 01493 filed Feb. 7, 2003, Mar. 20, 2003, Jun. 19, 2003, Jun. 19, 2003, Jun. 19, 2003, Jun. 19, 2003, Oct. 10, 2003 and Oct. 10, 2003, respectively, and U.S. provisional application Nos. 60/445,686, 60/456,470, 60/480,024, 60/480,096, 60/480,102, 60/480,107, 60/510,406, and 60/510,411, filed Feb. 7, 2003, Mar. 21, 2003, Jun. 20, 2003, Jun. 20, 2003, Jun. 20, 2003, Jun. 20, 2003, Oct. 10, 2003, and Oct. 10, 2003, respectively, the contents of which are fully incorporated herein by reference.

FIELD OF THE INVENTION

The present invention relates to a certain class of serine proteases that are stable and/or relatively unaffected by copper, as well as to DNA encoding these proteases, their recombinant production, and their use in animal feed and detergents.

BACKGROUND OF THE INVENTION

The cloning and expression of a protease derived from *Metarhizium anisopliae* is disclosed by Steven E. Screen and Raymond J. St. Leger in The Journal of Biological Chemistry, Vol. 275, No. 9, 2000, pp 6689-6694. The nucleotide sequence, chy1, thereof is shown in the sequence listing as SEQ ID NO: 3, and the deduced amino acid sequence, CHY1, as SEQ ID NO: 4 (TREMBL:Q9Y843).

Proteases derived from *Nocardiopsis* sp. NRRL 18262 and *Nocardiopsis dassonvillei* NRRL 18133 are described in WO 88/03947. The DNA and amino acid sequences of the protease derived from *Nocardiopsis* sp. NRRL 18262 are shown in DK patent application no. 1996 00013. WO 01/58276 describes the use in animal feed of acid-stable proteases related to the protease derived from *Nocardiopsis* sp. NRRL no. 18262. JP 2255081 A describes a protease purified from *Nocardiopsis* sp. FERM P-1-508. GDR patent no. DD 2,004, 328 discloses a protease derived from *Nocardiopsis dassonvillei* ZIMET 43647.

It is an object of the present invention to provide alternative proteases for various industrial uses, for example for use in animal feed and/or detergents.

SUMMARY OF THE INVENTION

The invention relates to a protease of peptidase family S2A or S1E which i) has a residual activity of at least 0.80 after incubation for 164 hours, at pH7 and 25° C., in assay buffer supplemented with 0.1% K-Sorbate, and in the presence of 1 mM $Cu^{2+}$, the residual activity being measured relative to the activity after 0 hours of incubation; and/or ii) has a relative activity of at least 0.66 in the presence of 1 mM $Cu^{2+}$, relative to a control without $Cu^{2+}$; wherein the activity measurements of i) and ii) are on the substrate Suc-AAPF-pNA, in assay buffer at pH7.0 and 25° C.; and wherein for the measurements of i), the protease has a purity by SDS-PAGE of at least 90%.

The invention also relates to isolated nucleic acid sequences encoding this protease and to nucleic acid constructs, vectors, and host cells comprising the nucleic acid sequences as well as methods for producing and using the protease.

BRIEF DESCRIPTION OF DRAWINGS

FIG. 1 is a multiple alignment of the mature peptide part of proteases derived from *Nocardiopsis* sp. NRRL 18262 (Protease 10, amino acids 1-188 of SEQ ID NO: 2), *Metarhizium anisopliae* (*Metarhizium* protease, amino acids 1-188 of SEQ ID NO: 4), *Nocardiopsis prasina* DSM 15648 (Protease 11, amino acids 1-188 of SEQ ID NO: 6), *Nocardiopsis prasina* DSM 15649 (Protease 35, amino acids 1-188 of SEQ ID NO: 8), *Nocardiopsis alba* DSM 15647 (Protease 08, amino acids 1-188 of SEQ ID NO: 10), *Nocardiopsis dassonvillei subsp. dassonvillei* DSM 43235 (Protease 18, amino acids 1-188 of SEQ ID NO: 12), and *Brachysporiella gayana* CGMCC 0865 (*Brachysporiella* protease, amino acids 1-186 of SEQ ID NO: 14).

DETAILED DESCRIPTION OF THE INVENTION

A description of serine proteases of peptidase families S2A and S1E is included in the section headed "polypeptides having protease activity."

Stability and Inhibition in the Presence of Copper

The invention relates to proteases which are i) relatively stable in the presence of $Cu^{2+}$, and/or ii) inhibited by $Cu^{2+}$ to a relatively low extent.

Feature i) is determined as residual (=rest, or remaining) enzyme activity after having incubated the enzyme for 164 hours, at pH7 and 25° C., in assay buffer supplemented with 0.1% K-Sorbate (for preservation purposes), and in the presence of 1 mM $Cu^{2+}$. The residual activity is measured relative to the activity after 0 hours of incubation. For the protease of the invention, the residual activity is at least 0.80 (=80%).

Protease activity is measured using the substrate Suc-AAPF-pNA, in assay buffer at pH7.0 and 25° C. For more details, please refer to the pNA assay described in Example 4, which also describes in detail the determination according to i) and ii).

It is presently contemplated that the purity of the protease tested may influence these stability results, and therefore the protease, at least when analyzed for stability according to i), preferably is at least 90% pure as measured by SDS-PAGE. A procedure for determining purity by SDS-PAGE is disclosed in Example 2. In particular embodiments, the purity by SDS-PAGE is at least 91%, 92%, 93%, 94%, or at least 95%. In alternative embodiments, the absorption purity (see Example 3), in particular for the purposes of test i), corresponds to an $A_{280}/A_{280}$ ratio of at least 1.40, or at least 1.42, 1.44, 1.46, 1.48, 1.50, 1.60, or at least 1.70.

Feature ii) is determined as the enzyme activity in the presence of 1 mM $Cu^{2+}$, relative to the activity of the same enzyme under the same conditions, except for the presence of $Cu^{2+}$. For the protease of the invention, this relative activity is at least 0.66 (=66%). For the purposes of feature ii), enzyme (protease) activity is measured as described above.

In particular embodiments of the proteases of the invention, the residual activity according to i) is at least 0.81, 0.82, 0.83, 0.84, 0.85, 0.86, 0.87, 0.88, 0.89, 0.90, 0.91, 0.92, 0.93, 0.94, 0.95, 0.96, or at least 0.97.

In alternative embodiments, the residual activity according to i) is at least 0.76, 0.77, 0.78, or 0.79. In other alternative embodiments, the residual activity according to i) is determined after incubation for 116 hours, in which case the residual activity for proteases of the invention is at least 0.84, with the same preferred ranges as listed above (from of at least 0.85 and upwards). In still further alternative embodiments, the residual activity according to i) is determined after incubation for 188.6 hours, in which case the residual activity for proteases of the invention is at least 0.73, with the same preferred ranges as listed above (from of at least 0.76 and upwards, plus the following: or at least 0.74, or at least 0.75).

In another set of particular embodiments of the proteases of the invention, the relative activity according to ii) is at least 0.67, 0.68, 0.69, 0.70, 0.71, 0.72, 0.73, 0.74, 0.75, 0.76, 0.77, 0.78, 0.79, 0.80, 0.81, or at least 0.82.

In an alternative embodiment, the substrate Boc-VLGR-pNA is used instead of Suc-AAPF-pNa for the activity measurements—according to i) and/or ii).

Results of stability and inhibition studies according to features i) and ii), respectively, are shown in Tables 2 and 1, respectively, of Example 4. From these tables it is clear that the proteases designated Protease 18 and *Brachysporiella* protease are the only proteases tested which fulfil feature i), whereas feature ii) is fulfilled for all proteases tested, except for the known proteases designated Protease 10 and *Metarhizium* protease.

A closer look at Table 1 reveals that Protease 18 and Protease 08 form a very interesting sub-group with a distinctly higher relative activity in the presence of copper (both with a relative activity above 0.80). However, the *Brachysporiella* protease is also very good (close to a relative activity of 0.70). This means that the two tests i) and ii) identify these three proteases as particularly interesting.

Before moving to consider potential structural elements that could explain the effects observed, here first some guidelines as to numbering of the amino acid residues in the various proteases tested, and instructions how to deduce corresponding amino acid residues in the various backbones.

Amino Acid Residue Numbering

In the present context, for the purposes of identifying corresponding amino acid residues in various proteases, reference is had to the numbering of the amino acid residues in the mature part (amino acids 1-188) of SEQ ID NO: 2, Protease 10, starting with A1 and ending with T188. FIG. 1 shows, in alignment clusters of 10 residues, the numbers of the last amino acid residue of each of such cluster, viz. in the top rows of the alignment. For example, the number "10" means that the last amino acid residue of Protease 10 in this first cluster of 10 residues, "T," is amino acid residue number 10 in the mature Protease 10 amino acid sequence. As another example, the number "145" means that the last amino acid residue of Protease 10 in this last cluster of residues in the third row of the alignment of FIG. 1, which is a "G," is residue number 145 in the mature Protease 10 amino acid sequence. This numbering is identical to the numbering of SEQ ID NO: 2, however not necessarily identical to the numbering of SEQ ID NOs: 4, 6, 8, 10, 12, and 14, the reason being that for the purposes of identifying corresponding amino acid residues in various proteases, a uniform numbering is used based on Protease 10. The procedure for assigning a uniform numbering is further described below.

For each of the amino acid residues of Protease 10, a "corresponding" residue can be identified in each of the other six proteases shown in FIG. 1, because "corresponding" residues are simply those that are placed one above the other, or on top of each other, in the alignment of FIG. 1. For example, the tenth amino acid residue, T, of Protease 10 (T10 of SEQ ID NO: 2) corresponds to Y10 of SEQ ID NOs: 4 and 12; to T10 of SEQ ID NOs: 6, 8 and 10; and to V8 of SEQ ID NO: 14. In the present context, however, for all purposes except for Sequence Listing purposes, these residues are all assigned the same number, because they qualify as "corresponding residues," and the number assigned is that of the corresponding residue in Protease 10, viz. residue number 10. Accordingly, T10 of Protease 10 corresponds to Y10, T10, T10, T10, Y10, and V10, of the *Metarhizium* protease, Protease 11, Protease 35, Protease 08, Protease 18, and the *Brachysporiella* protease, respectively. When nothing else is stated, this numbering is used hereinafter.

The multiple alignment of FIG. 1, in certain rows, at certain positions, includes gaps, which can be considered as deletions of amino acid residues. In the present context, the gaps, or the deleted amino acid residues, are numbered by assigning to each gap lower case letters in alphabetical order, viz. a, b, c, d, - - - t, u, v, x, y, z. Should more than 25 of such designations be needed, the numbering would continue with aa, bb, cc etc. For example, the gap between G12 and G13 of Protease 10 corresponds to a deletion of two amino acid residues in positions 12a, and 12b. Accordingly, the corresponding residues in the *Metarhizium protease (SEQ ID NO: 4)* shown in the second row of FIG. 1 are designated R12a, and S12b. By analogy, the successive amino acid residues FPGSA in the *Metarhizium* protease corresponding to FPGN in positions 57-60 of Protease 10 are numbered as follows: F57, P58, G59, S59a, and A60; position 59a being equivalent to a deletion of an amino acid in Protease 10.

Two of the proteases included in the alignment of FIG. 1 comprise C-terminal extensions as compared to Protease 10, viz. the *Metarhizium* protease and the *Brachysporiella* protease. The amino acids of such extensions are numbered as is usual in the art continuing from no. 188, viz. 189, 190, 191 and so forth. For example, the last amino acid of the *Metarhizium* protease is referred to as A189.

Another protease having an amino acid sequence with a mature peptide part of SEQ ID NO: X may be added to the alignment of FIG. 1 as follows:

The percentage of identity of SEQ ID NO: X to each of the seven proteases of FIG. 1 (each of the mature peptide parts of SEQ ID NOs: 2, 4, 6, 8, 10, 12 and 14) is determined using the "Align" program as described below. Seven pairwise alignments are thereby produced. The sequence with the highest degree of identity to SEQ ID NO: X is selected as a model protease. If there are more candidate model proteases, you select the one which is listed first in the FIG. 1 alignment. If, for example, SEQ ID NO: X would have the following percentage of identities to SEQ ID NOs: 2, 4, 6, 8, 10, 12, and 14: 45%, 55%, 50%, 65%, 65%, 45%, and 40%, respectively, then SEQ ID NO: 8 should be selected as the model protease. As a next step, using the pairwise alignment of SEQ ID NO: X to SEQ ID NO: 8, SEQ ID NO: X is pasted (or it could simply be written) onto the alignment of FIG. 1 as the bottom row, ensuring that corresponding amino add residues (here "corresponding" refers to the pairwise alignment of SEQ ID NO: X and SEQ ID NO: 8) are placed above each other.

While the FIG. 1 alignment remains unaffected by this procedure of adding a new sequence to it, the described procedure may give rise to gaps in SEQ ID NO: X; "loops" in SEQ ID NO: X, and/or N- or C-terminal extensions of SEQ ID NO: X, as compared to Protease 10 of FIG. 1.

As regards the numbering of such positions with a view to identifying corresponding amino acid residues in SEQ ID NO: X, the gaps and the C-terminal extensions are dealt with as described above. N-terminal extensions, if any, are numbered as is usual in the art, −1, −2, −3 and so forth ("−" meaning "minus"). For example, if SEQ ID NO: X when added to the alignment of FIG. 1 would start with the sequence AL1 positioned before the N-terminal amino acid A1 of Protease 10, these would be numbered A-3, L-2, and I-1, respectively. As regards the loops, if any, this corresponds to SEQ ID NO: X having "excess" amino acid residues, which the alignment of FIG. 1 does not make room for. Typographically, such excess residues are transferred onto a next row, but they are of course considered to be included in the multiple alignment, and are numbered by analogy to what is described above for the numbering of gaps (using the denotations a, b, c etc.). For example, the pairwise alignment of SEQ ID NO: X and SEQ ID NO: 8 could include the following part:

```
(part of SEQ ID NO: 8)      FAAT-----NAAGQP
(part of SEQ ID NO: X)      YAVSCRTAKNAACQP,
```

The amino acid residues FAATNAAGQP of Protease 08 (SEQ ID NO: 8) have alignment numbers 19 to 28 and these turn up to correspond, in the pairwise alignment, to the following amino acid residues of SEQ ID NO: X: YAVSCR-TAKNAACQP. For the present purposes, the amino acid residues of SEQ ID NO: X would have to be numbered as follows: Y19, A20, V21, S22, C22a, R22b, T22c, A22d, K22e, N23, A24, A25, C26, Q27, P28.

In the alignment of FIG. 1 this may be written as follows:

```
(part of SEQ ID NO: 8)      FAATNAAGQP
(part of SEQ ID NO: X)      YAVSNAACQP,
                       CRTAK 22e
```

In particular alternative embodiments, the pairwise alignments referred to above are produced using the complete CDS parts (including in addition to the mature peptide parts any signal peptide parts, and/or propeptide parts) of SEQ ID NOs: 2, 4, 6, 8, 10, 12 and 14.

The following are examples of the denotation used herein to characterize proteases:

Expressions like the following:

"A protease comprising an amino acid sequence which, when aligned according to FIG. 1, comprises V166, wherein the numbering of the amino acid residue corresponds to the numbering of Protease 10 (amino acids 1-188 of SEQ ID NO: 2)"

mean that the amino acid sequence of the protease in question, when added to the multiple alignment of FIG. 1 as described above, in position number 166 (which refers to the alignment number deduced as described above) has a V.

Expressions like "at least one of (L114 or Y114); (S121 or D121); (Q130 or M130); (N162 or T162 or S162); (S163 or R163); E174; and/or (S177 or E177)," are used about a protease that fulfills either of (at least one of) the criteria separated by semicolons (;). This is the case, for example, for a protease having Y114, or S121, or M130, or E174, but also for a protease having L114 and D121.

Expressions like:

"A protease comprising at least one of the following:
a) (T120+R122+T127+Y129), (T120+N122+P127+F129), or (T120+S122+T127+Q129); and/or
b) (T91+T176+I179+N180), (S91+N176+L179+E180), or (S91+N176L179S180),"

are used about a protease that fulfills all of the criteria separated by plusses (+) within at least one of the six brackets. This is the case, for example, for Protease 18 having T120, R122, T127, and Y129 (first bracket in a)). This protease, by the way, also comprises T91, T176, I179 and N180 (first bracket in b)).

Expressions like "(H35+D61+S143)," are used about at protease comprising H35, D61 and S143 (active site amino acid residues).

Structural Considerations Relating to Cu

The surprising findings of the present invention as regards the varying influence of copper on the various enzymes tested has prompted some research with a view to defining, if possible, structural elements that could explain the observed differences. Two potential copper binding sites (Site Nos. I and II as shown in the below Table) were identified, of which Site No. I is expected to be the most important site:

| Protease/Residue No. | Site No. I | | | | Site No. II | | | | Parts of SEQ ID NO: |
|---|---|---|---|---|---|---|---|---|---|
| | 120 | 122 | 127 | 129 | 91 | 176 | 179 | 180 | |
| Protease 18 | T | R | T | Y | T | T | I | N | 12 |
| *Brachysporiella* | T | N | P | F | S | N | L | E | 14 |
| Protease 08 | T | S | T | Q | S | N | L | S | 10 |
| Protease 35 | S | S | T | T | H | T | V | N | 8 |
| Protease 11 | S | S | T | T | H | T | V | N | 6 |
| Protease 10 | S | S | T | T | H | T | V | N | 2 |
| *Metarhizium* | T | N | A | S | S | N | L | Q | 4 |

In the above Table, a double-line (=) is placed between those proteases that are relatively unaffected by copper, and those that are more negatively affected by copper (those above, and below, respectively, the double-line).

From this Table it appears as if the following combinations of residues of Site No. I are disadvantageous as regards the achievement of a high stability and/or a low inhibition by copper: a) (T120+N122+A127+S129), and b) (S120+S122+T127+T129).

By analogy, the following combinations of Site No. II residues may also be disadvantageous: a) (S91+N176+L179+Q180), and b) (H91+T176+V179+N180).

On the other hand, the following combinations of residues of Site Nos. I and II appear to be favourable:
a) (T120+R122+T127+Y129), (T120+N122+P127+F129), or (T120+S122+T127+Q129); and/or
b) (T91+T176+I179+N180), (S91+N176+L179+E180), or (S91+N176+L179S180), Other residues that may contribute to a structural explanation of the observed differences are the residues in position 51, 54, 86, 89, 99, 125, 130, 131, 135, 165, and 166. Therefore, in particular embodiments the protease of the invention does not comprise any of the following combinations of residues: a) (V51+Q54+A86 +A89+S99+E125+N130+M131+ T135+R165+T166), and not b) (T51+G54+P86+S89+S99+ Q125+S130+L131+S135+S165+R166). On the other hand, in additional particular embodiments, the protease of the invention comprises at least one of the following: T51; N54 or G54; Q86 or P86; T89 or F89; A99 or G99; Q125 or V125; S130 or G130; L131; N135 or S135; S165 or T165;V166 or S166. The expression "at least one" means one, two, three, four, five, six, seven, eight, nine, ten, or all eleven of these residues, in combination. For the purposes of the present invention, this definition of "at least one" is generally applicable, by analogy.

In alternative embodiments, the present invention explicitly relates to proteases as defined in this section without the functional features i) and ii) of claim 1 as filed, preferably proteases of peptidase family S2A or S1E.

Polypeptides having Protease Activity

Polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW).

Proteases are classified on the basis of their catalytic mechanism into the following groups: Serine proteases (S), Cysteine proteases (C), Aspartic proteases (A), Metalloproteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

The proteases of the invention are selected from the group consisting of:

(a) Serine proteases of peptidase family S2A according to the above Handbook; and (b) Serine proteases of peptidase family S1E as described in Biochem.J. 290:205-218 (1993) and in MEROPS protease database, release 6.20, Mar. 24, 2003, (www.merops.ac.uk). The database is described in Rawlings, N. D., O'Brien, E. A. & Barrett, A. J. (2002) MEROPS: the protease database. Nucleic Acids Res. 30, 343-346.

Peptidase family S2A represents the traditional way of classifying proteases. Nowadays, proteases traditionally classified as S2A proteases are often classified according to the MEROPS classification in peptidase family S1E.

In a particular embodiment, the protease is of peptidase family S2A. In another particular embodiment, the protease is of peptidase family S1E.

In alternative embodiments, the proteases of the invention are selected from the group consisting of:

(c) proteases belonging to the EC 3.4.-.- enzyme group; and (d) Serine proteases belonging to the S group of the above Handbook;

For determining whether a given protease is a Serine protease, a family S2A protease, and/or a family S1E protease, reference is made to the above references and the principles indicated therein. Such determination can be carried out for all types of proteases, be it naturally occurring or wild-type proteases; or genetically engineered or synthetic proteases.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 20, 25, 30, 35, 37, 40, 45, 50, 55, 60, 65, 70 or 80° C.

Examples of protease substrates are casein, such as Azurine-Crosslinked Casein (AZCL-casein). For the purposes of this invention, the so-called pNA Assay is a preferred assay, and a preferred substrate is Suc-AAPF-pNA.

There are no limitations on the origin of the protease of the invention. Thus, the term protease includes not only natural or wild-type proteases obtained from microorganisms of any genus, but also any mutants, variants, fragments etc. thereof exhibiting protease activity, as well as synthetic proteases, such as shuffled proteases, and consensus proteases. Such genetically engineered proteases can be prepared as is generally known in the art, e.g. by Site-directed Mutagenesis, by PCR (using a PCR fragment containing the desired mutation as one of the primers in the PCR reactions), by shuffling, or by Random Mutagenesis. The preparation of consensus proteins is described in e.g. EP 897985. The term "obtained from" as used herein in connection with a given source shall mean that the polypeptide encoded by the nucleic acid sequence is produced by the source or by a cell in which the nucleic acid sequence from the source is present. In a preferred embodiment, the polypeptide is secreted extracellularly.

In a specific embodiment, the protease is a low-allergenic variant, designed to invoke a reduced immunological response when exposed to animals, including man. The term immunological response is to be understood as any reaction by the immune system of an animal exposed to the protease. One type of immunological response is an allergic response leading to increased levels of IgE in the exposed animal. Low-allergenic variants may be prepared using techniques known in the art. For example the protease may be conjugated with polymer moieties shielding portions or epitopes of the protease involved in an immunological response. Conjugation with polymers may involve in vitro chemical coupling of polymer to the protease, e.g. as described in WO 96/17929, WO 98/30682, WO 98/35026, and/or WO 99/00489. Conjugation may in addition or alternatively thereto involve in vivo coupling of polymers to the protease. Such conjugation may be achieved by genetic engineering of the nucleotide sequence encoding the protease, inserting consensus sequences encoding additional glycosylation sites in the protease and expressing the protease in a host capable of glycosylating the protease, see e.g. WO 00/26354. Another way of providing low-allergenic variants is genetic engineering of the nucleotide sequence encoding the protease so as to cause the protease to self-oligomerize, effecting that protease monomers may shield the epitopes of other protease monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the protease by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

In a particular embodiment, the polypeptide of the invention comprises an amino acid sequence having protease activity and having a degree of identity of at least 40% to amino acids 1 to 186 of SEQ ID NO: 14, and/or to amino acids 1-188 of (SEQ ID NOs: 12, 10, 8, 6, 4 or 2) (hereinafter "homologous polypeptides"). In further particular embodiments, the degree of identity is at least about 42%, 44%, 46%, 48%, 50%, 52%, 54%, 56%, 58%, 60%, 62%, 63%, 64%, 66%, 68%, 70%, 72%, 75%, 77%, 80%, 82%, 85%, 87%, 90%, 92%, 95%, or at least about 97%. In another alternative embodiment, any of the above degrees of identity is relative to any of the complete CDS parts of SEQ ID NOs: 14, 12, 10, 8, 6, 4 or 2, e.g. amino acids −189 to 186 of SEQ ID NO: 2. In particular embodiments, the polypeptides of the invention i) have; or ii) consist of an amino acid sequence with any of the degrees of identity as mentioned above.

For the purposes of the present invention, the degree of identity between two amino acid sequences, as well as the degree of identity between two nucleotide sequences, is determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotide.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183: 63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

In a particular embodiment, the mature peptide parts, or predicted or expected mature peptide parts, of the two amino acid sequences are used for the alignment.

In the alternative, the degree of identity between two amino acid sequences may be determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters are Ktuple=1, gap penalty=3, windows=5, and diagonals=5. The degree of identity between two nucleotide sequences may be determined using the same algorithm and software package as described above with the following settings: Gap penalty of 10, and gap length penalty of 10. Pairwise alignment parameters are Ktuple=3, gap penalty=3 and windows=20.

In a particular embodiment, the homologous polypeptides have an amino acid sequence that differs by ten, or by nine, or by eight, or by seven, or by six, or by five amino acids. In another particular embodiment, the homologous polypeptides differ by four, or by three, or by two amino acids, or by one amino acid from amino acids 1 to 186 of SEQ ID NO: 14, or from amino acids 1-188 of (SEQ ID NOs: 12, 10, 8, 6, 4 or 2). In alternative embodiments, the homologous polypeptides have an amino acid sequence that differs by forty, thirty-five, thirty, twenty-five, twenty, or fifteen amino acids from amino acids 1 to 186 of SEQ ID NO: 14, or from amino acids 1-188 of (SEQ ID NOs: 12, 10, 8, 6, 4 or 2).

In a particular embodiment, the polypeptides of the present invention comprise the amino acid sequence of amino acids 1 to 186 of SEQ ID NO: 14, or amino acids 1-188 of (SEQ ID NOs: 12, 10, 8, 6, 4 or 2), or allelic variants thereof; or fragments thereof that have protease activity.

In another preferred embodiment, the polypeptides of the present invention consist of amino acids 1 to 186 of SEQ ID NO: 14, or of amino acids 1-188 of (SEQ ID NOs: 12, 10, 8 or 6), or allelic variants thereof; or fragments thereof that have protease activity.

A fragment is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The present invention also relates to isolated polypeptides having protease activity and which are encoded by nucleic acid sequences which hybridize under very low, or low, or medium, or medium-high, or high, or very high stringency conditions with a nucleic acid probe which hybridizes under the same conditions with (a) nucleotides 726-1283 of SEQ ID NO: 13, nucleotides 499-1062 of SEQ ID NO: 11, nucleotides 502-1065 of SEQ ID NO: 9, nucleotides 496-1059 of SEQ ID NO: 7, nucleotides 496-1059 of SEQ ID NO: 5, nucleotides 559-1122 of SEQ ID NO: 3, and/or nucleotides 900-1466 of SEQ ID NO: 1; (b) a subsequence of (a), or (c) a complementary strand of (a), or (b) (J. Sambrook, E. F. Fritsch, and T. Maniatis, 1989, Molecular Cloning, A Laboratory Manual, 2nd edition, Cold Spring Harbor, N.Y.). In one particular embodiment the nucleic acid probe is selected from amongst the nucleic acid sequences of (a), (b), or (c) above. Nucleotides 726-1283 of SEQ ID NO: 13, nucleotides 499-1062 of SEQ ID NO: 11, nucleotides 502-1065 of SEQ ID NO: 9, nucleotides 496-1059 of SEQ ID NO: 7, nucleotides 496-1059 of SEQ ID NO: 5, nucleotides 559-1122 of SEQ ID NO: 3, and/or nucleotides 900-1466 of SEQ ID NO: 1, corresponding to the respective mature peptide parts, are preferred probes.

The subsequence may be at least 100 nucleotides, or in another embodiment at least 200 nucleotides. Moreover, the subsequence may encode a polypeptide fragment that has protease activity.

The nucleic acid sequences listed under (a) or (b) above, as well as the corresponding amino acid sequences or fragments thereof, may be used to design a nucleic acid probe to identify and clone DNA encoding polypeptides having protease activity from strains of different genera or species according to methods well known in the art. In particular, such probes can be used for hybridization with the genomic DNA or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labelled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA that hybridizes with the probes described above and which encodes a polypeptide having protease activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a homologous clone or homologous DNA, the carrier material is used in a Southern blot. For purposes of the present invention, hybridization indicates that the nucleic acid sequence hybridizes to a labelled nucleic acid probe corresponding to the selected nucleic acid sequence, its complementary strand, or a subsequence thereof, under very low to very high stringency conditions. Molecules to which the nucleic acid probe hybridizes under these conditions may be detected using X-ray film.

In a particular embodiment, the nucleic acid probe is nucleotides 726-1283 of SEQ ID NO: 13, nucleotides 499-1062 of SEQ ID NO: 1 1, nucleotides 502-1065 of SEQ ID NO: 9, nucleotides 496-1059 of SEQ ID NO: 7, nucleotides 496-1059 of SEQ ID NO: 5, nucleotides 559-1122 of SEQ ID NO: 3, and/or nucleotides 900-1466 of SEQ ID NO: 1. In another embodiment, the nucleic acid probe is a nucleic acid sequence which encodes the amino acid sequences corresponding to any or the nucleotide sequences listed in the previous sentence.

In another preferred embodiment, the nucleic acid probe is the nucleic acid sequence, or preferably the mature polypeptide coding region thereof, which is contained in the plasmid which is contained in *Escherichia coli* DSM 15509, wherein the nucleic acid sequence encodes a polypeptide having protease activity.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes about 15 nucleotides to about 70 nucleotides in length, the carrier material is washed once in 6×SSC plus 0.1% SDS for 15 minutes and twice each for 15 minutes using 6×SSC at 5° C. to 10° C. below the calculated $T_m$.

The present invention also relates to variants of the polypeptide having amino acids 1 to 186 of SEQ ID NO: 14, and/or amino acids 1-188 of (SEQ ID NOs: 12, 10, 8, 6, 4 or 2) comprising a substitution, deletion, and/or insertion of one or more amino acids.

The amino acid sequences of the variant polypeptides may differ from the amino acid sequence of amino acids 1 to 186, −170 to 186, or −189 to 186 of SEQ ID NO: 14, or from the corresponding parts of any one of SEQ ID NOs: 12, 10, 8, 6, 4 or 2, by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a particular embodiment, the polypeptides of the invention and for use according to the invention are acid-stable. For the present purposes, the term acid-stable means that the residual activity after 2 hours of incubation at pH 3.0 and 37° C., is at least 20%, as compared to the residual activity of a corresponding sample incubated for 2 hours at pH 9.0 and 5° C. In a particular embodiment, the residual activity is at least 22%, 24%, 25% or at least 26%. In the alternative, the acid-stability definition refers to a residual activity of at least 50%, or 60%, or 70% when measured at pH 3.5 and 37° C., as compared to the residual activity of a corresponding sample incubated for 2 hours at pH 9.0 and 5° C. A suitable assay for determining acid stability is disclosed in Example 2C of WO 01/58276.

In another particular embodiment, the polypeptides of the invention and for use according to the invention have a relative activity at pH 7.0 of at least 0.2, 0.3, 0.4, or at least 0.5. The pH-profile test of Example 2B of WO 01/58276 is a suitable assay.

The polypeptide of the invention and for use according to the invention may be a bacterial or fungal polypeptide. The fungal polypeptide may be derived from a filamentous fungus or from a yeast.

In particular embodiments, the polypeptide of the invention is i) a fungal protease; ii) a protease derived from the phylum Ascomycota; iii) the subphylum Pezizomycotina; iv) the class Sordariomycetes; v) the order Sordariales; vi) the family Annulatascaceae; vii) the genus Ascotaiwania and/or *Brachysporiella* (*Brachysporiella* being the anamorphic (asexual) state of this fungus, and Ascotaiwania being the teleomorphic or sexual state); and/or viii) a protease derived from a strain of Ascotaiwania and/or *Brachysporiella*, for example *Ascotaiwania mitriformis*, *Ascotaiwania sawada*, *Brachysporiella gayana*, and *Brachysporiella* sp., for example *Brachysporiella gayana* CGMCC 0865, such as a polypeptide with the amino acid sequence of amino acids 1 to 186, −170 to 186, or −189 to 186 of SEQ ID NO: 14.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

The above taxonomy is mainly according to Ranghoo, V. M., Goh, T. K. & Hyde, K. D. 1999. New observations on *Monotosporella rhizoidea*. Mycosciences 40: 377-382; and Sivichai, S., Hywel-Jones, N. & J. E. B. G. 1998, Liginicolous freshwater Ascomycota from Thailand: I. *Ascotaiwania sawada* and its anamorph state *Monotosporella*. Mycosciense 39: 307-311.

In another particular embodiment, the polypeptide of the invention is i) a bacterial protease; ii) a protease derived from the phylum Actinobacteria; iii) the class Actinobacteria; iv) the order Actinomycetales v) the family Nocardiopsaceae; vi) the genus *Nocardiopsis*; and/or a protease derived from vii) *Nocardiopsis* species such as *Nocardiopsis alba*, *Nocardiopsis antarctica*, *Nocardiopsis prasina*, *Nocardiopsis composta*, *Nocardiopsis exhalans*, *Nocardiopsis halophila*, *Nocardiopsis halotolerans*, *Nocardiopsis kunsanensis*, *Nocardiopsis listeri*, *Nocardiopsis lucentensis*, *Nocardiopsis metallicus*, *Nocardiopsis synnemataformans*, *Nocardiopsis trehalosi*, *Nocardiopsis tropica*, *Nocardiopsis umidischolae*, *Nocardiopsis xinjiangensis*, or *Nocardiopsis dassonvillei*, for example:

*Nocardiopsis dassonvillei* DSM 43235, such as Protease 18, a polypeptide with the amino acid sequence of amino acids 1 to 188, or −166 to 188, of SEQ ID NO: 12;

*Nocardiopsis alba* DSM 15647, such as a Protease 08, a polypeptide with the amino acid sequence of amino acids 1 to 188, or −167 to 188, of SEQ ID NO: 10;

*Nocardiopsis prasina* DSM 15649, such as Protease 35, a polypeptide with the amino acid sequence of amino acids 1 to 188, or −165 to 188, of SEQ ID NO: 8;

*Nocardiopsis prasina* DSM 15648, such as Protease 11, a polypeptide with the amino acid sequence of amino acids 1 to 188, or −165 to 188, of SEQ ID NO: 6.

These four proteases, together with the protease from *Brachysporiella gayana* CGMCC 0865, the *Brachysporiella* protease, such as a polypeptide with the amino acid sequence of amino acids 1 to 186, −170 to 186, or −189 to 186 of SEQ ID NO: 14, form a particular embodiment of the invention. A subgroup consisting of Protease 18, Protease 08, and the *Brachysporiella* protease is another particular embodiment of the invention, and a subgroup consisting of the *Brachysporiella* protease and Protease 18 is a still further particular embodiment of the invention.

The above taxonomy is according to the chapter: The road map to the Manual by G. M. Garrity & J. G. Holt in Bergey's Manual of Systematic Bacteriology, 2001, second edition, volume 1, David R. Bone, Richard W. Castenholz. Strains of these species are readily accessible to the public in a number of culture collections, such as the American Type Culture Collection (ATCC), Deutsche Sammlung von Mikroorganismen und Zelikulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic DNA or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

A screening for proteases which are not affected, or relatively un-affected, by copper may be conducted by incorporating desired levels of $Cu^{2+}$ and/or $Cu^{+}$ in appropriate screening media and selecting the most potent protease producers. The expression "potent" of course refers to protease activity, which may be estimated using any suitable protease screening procedure, e.g. based on the size of clearing zones in solid media containing skim-milk. Examples of desired levels of copper are up to 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, or up to 10000 ppm Cu. The content of Cu should be at least 0.2, 0.4, 0.6, 0.8, 1.0, 2, 3, 4, 5, 6, 7, 8, 9 or at least 10 ppm. The expression ppm means parts per million (w/w), e.g. mg/kg, and can be converted to molar concentrations of Cu using its atomic weight (approx. 63.5), as is known in the art, e.g.1 mM Cu corresponds to 63.5 ppm Cu.

In a particular embodiment, the protease of the invention is isolated and/or purified. As defined herein, an "isolated" polypeptide is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

In particular embodiments, the polypeptide of the invention does not encompass (i.e., excludes): a) amino acids −186 to 188, −167 to 188, or 1-188 of SEQ ID NO: 4; b) amino acids 1-188 of SEQ ID NO: 2; c) the protease from *Nocardiopsis dassonvillei* NRRL 18133 which is described in WO 88/03947, preferably having a Molecular Weight (MW) by SDS-PAGE of 20,500 Dalton, and isoelectric points, pI, of 9.15 and 8.2; d) the protease from *Nocardiopsis* sp. which is described in JP 2255081 A, preferably having a MW by SDS electrophoresis of 21,000 Da and an optimum pH of 10-12;

and/or e) the protease derived from the strain ZIMET 43647 of the species *Nocardiopsis dassonvillei* described by GDR patent no. DD 2,004,328.

Nucleic Acid Sequences

The present invention also relates to isolated nucleic acid sequences that encode a polypeptide of the present invention. Particular nucleic acid sequences of the invention are nucleotides 726-1283 of SEQ ID NO: 13, nucleotides 499-1062 of SEQ ID NO: 11, nucleotides 502-1065 of SEQ ID NO: 9, nucleotides 496-1059 of SEQ ID NO: 7, nucleotides 496-1059 of SEQ ID NO: 5. Another particular nucleic acid sequence of the invention is the sequence, preferably the mature polypeptide encoding region thereof, which is contained in the plasmid that is contained in the deposited microorganism *Escherichia coli* DSM 15509. The present invention also encompasses nucleic acid sequences which encode a polypeptide having the amino acid sequence of amino acids 1 to 186 of SEQ ID NO: 14, and/or amino acids 1-188 of (SEQ ID NOs: 12, 10, 8, 6, 4 or 2), which differ from the corresponding nucleotide sequences by virtue of the degeneracy of the genetic code. The present invention also relates to subsequences of the above nucleotide sequences which encode fragments of the above amino acid sequences that have protease activity.

In a subsequence one or more nucleotides from the 5' and/or 3' end have been deleted. Preferably, a subsequence contains at least 150, 190 or at least 225 nucleotides, more preferably at least 300 nucleotides, even more preferably at least 375, 450, 500, 531, 600, 700, 800, 900, 1000, or 1100 nucleotides.

The present invention also relates to nucleotide sequences encoding proteases that are more stable in the presence of copper and/or less inhibited by copper, which have a degree of identity of at least 40% to nucleotides 726-1283 of SEQ ID NO: 13, nucleotides 499-1062 of SEQ ID NO: 11, nucleotides 502-1065 of SEQ ID NO: 9, nucleotides 496-1059 of SEQ ID NO: 7, nucleotides 496-1059 of SEQ ID NO: 5, nucleotides 559-1122 of SEQ ID NO: 3, and/or to nucleotides 900-1466 of SEQ ID NO: 1. In particular embodiments, the degree of identity is at least 42%, 45%, 47%, 50%, 52%, 55%, 57%, 60%, 62%, 64%, 65%, 67%, 70%,72%,75,77%, 80%, 82%, 85%, 87%, 90%, 92%, 95%, or at least 97%.

The present invention also relates to mutant nucleic acid sequences comprising at least one mutation in any of the above nucleotide sequences, in which the mutant nucleic acid sequence e ncodes a polypeptide which (i) consists of a ny of the corresponding a mino a cid sequences, or (ii) is a variant of any of the sequences of (i), wherein the variant comprises a substitution, deletion, and/or insertion of one or more amino acids, or (iii) is an allelic variant of any of the sequences of (i), or (iv) is a fragment of any of the sequences of (i).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Brachysporiella* (Ascotaiwania), or a strain of *Nocardiopsis*, or from other or related organisms and thus, for example, may be an allelic or species variant of the polypeptide encoding regions of the nucleic acid sequences.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, allergenicity, or the like. The variant sequence may be constructed on the basis of the nucleic acid sequence presented as the polypeptide encoding part of SEQ ID NO: 1, 3, 5, 7, 9, 11 or 13, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the protease, or by introduction of nucleotide substitutions which may give rise to a different amino acid sequence. For a general description of nucleotide substitution, see, e.g., Ford et al., 1991, Protein Expression and Purification 2: 95-107. Low-allergenic polypeptides can e.g. be prepared as described above.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for protease activity to identify amino acid residues that are critical to the activity of the molecule. Sites of substrate-protease interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with nucleotides 726-1283 of SEQ ID NO: 13, nucleotides 499-1062 of SEQ ID NO: 11, nucleotides 502-1065 of SEQ ID NO: 9, nucleotides 496-1059 of SEQ ID NO: 7, nucleotides 496-1059 of SEQ ID NO: 5, nucleotides 559-1122 of SEQ ID NO: 3, and/or nucleotides 900-1466 of SEQ ID NO: 1; or their complementary strands; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 726-1283 of SEQ ID NO: 13, nucleotides 499-1062 of SEQ ID NO: 11, nucleotides 502-1065 of SEQ ID NO: 9, nucleotides 496-1059 of SEQ ID NO: 7, nucleotides 496-1059 of SEQ ID NO: 5, nucleotides 559-1122 of SEQ ID NO: 3, and/or nucleotides 900-1466 of SEQ ID NO: 1; (ii) a subsequence of (i), or (iii) a complementary strand of (i), or (ii); and (b) isolating the nucleic acid sequence. The subsequence is preferably a sequence of at least 100 nucleotides such as a sequence that encodes a polypeptide fragment which has protease activity.

In particular embodiments, the nucleic acid sequence of the invention does not encompass (i.e., excludes): a) nucleotides 1-1122 and/or 559-1122 of SEQ ID NO: 3; and/or b) nucleotides 1-1596 and/or 900-1466 of SEQ ID NO: 1.

Methods for Producing Mutant Nucleic Acid Sequences

The present invention further relates to methods for producing a mutant nucleic acid sequence, comprising introducing at least one mutation into the mature polypeptide coding sequence of nucleotides 726-1283 of SEQ ID NO: 13, nucleotides 499-1062 of SEQ ID NO: 11, nucleotides 502-1065 of SEQ ID NO: 9, nucleotides 496-1059 of SEQ ID NO: 7, nucleotides 496-1059 of SEQ ID NO: 5, nucleotides 559-1122 of SEQ ID NO: 3, and/or nucleotides 900-1466 of SEQ ID NO: 1, or a subsequence thereof, wherein the mutant nucleic acid sequence encodes a polypeptide which consists of the corresponding amino acids sequences; or fragments thereof which have protease activity.

The introduction of a mutation into the nucleic acid sequence to exchange one nucleotide for another nucleotide may be accomplished by site-directed mutagenesis using any of the methods known in the art. Particularly useful is the procedure that utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences that direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion. "Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence that directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components that are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence that is recognized by a host cell for expression of the nucleic acid sequence. The promoter sequence contains transcriptional control sequences that mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, Aspergillus nidulans acetamidase, and Fusarium oxysporum trypsin-like protease (WO 96/00787), as well as the NA2-tpi promoter (a hybrid of the promoters from the genes for Aspergillus niger neutral alpha-amylase and Aspergillus oryzae triose phosphate isomerase), and mutant, truncated, and hybrid promoters thereof.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH2/GAP), and Saccharomyces cerevisiae 3-phosphoglycerate kinase. Other useful promoters for yeast host cells are described by Romanos et al., 1992, Yeast 8: 423-488.

Examples of suitable promoters for directing the transcription of the nucleic acid constructs of the present invention, especially in a bacterial host cell, are the promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophilus maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for Aspergillus oryzae TAKA amylase, Aspergillus niger glucoamylase, Aspergillus nidulans anthranilate synthase, Aspergillus niger alpha-glucosidase, and Fusarium oxysporum trypsin-like protease.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

Preferred terminators for bacterial host cells, such as a Bacillus host cell, are the terminators from Bacillus licheniformis alpha-amylase gene (amyL), the Bacillus stearothermophilus maltogenic amylase gene (amyM), or the Bacillus amyloliquefaciens alpha-amylase gene (amyQ).

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for Aspergillus oryzae TAKA amylase, Aspergillus niger glucoamylase, Aspergillus nidulans anthranilate synthase, Fusarium oxysporum trypsin-like protease, and Aspergillus niger alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, Bacillus stearothermophilus alpha-amylase, Bacillus licheniformis subtilisin, Bacillus licheniformis alpha-amylase, Bacillus stearothermophilus neutral proteases (nprT, nprS, nprM), and Bacillus subtilis prsA. Further signal peptides are described by Simonen and Palva, 1993, Microbiological Reviews 57: 109-137.

Effective signal peptide coding regions for filamentous fungal host cells are the signal peptide coding regions obtained from the genes for Aspergillus oryzae TAKA amylase, Aspergillus niger neutral amylase, Aspergillus niger glucoamylase, Rhizomucor miehei aspartic proteinase, Humicola insolens cellulase, and Humicola lanuginosa lipase.

Useful signal peptides for yeast host cells are obtained from the genes for Saccharomyces cerevisiae alpha-factor and Saccharomyces cerevisiae invertase. Other useful signal peptide coding regions are described by Romanos et al., 1992, supra.

In a preferred embodiment, the signal peptide coding region is selected from the signal peptide coding regions of SEQ ID NO: 1, 3, 5, 7, 9, 11 and 13.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained, e.g., from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

In a preferred embodiment, the propeptide coding region is selected from the propeptide coding regions of SEQ ID NO: 1, 3, 5, 7, 9, 11 and 13.

Where both signal peptide and propeptide regions are present at the amino terminus of a polypeptide, the propeptide region is positioned next to the amino terminus of a polypeptide and the signal peptide region is positioned next to the amino terminus of the propeptide region.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independently of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, Proceedings of the National Academy of Sciences USA 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The protease may also be co-expressed together with at least one other enzyme of interest for animal feed, such as phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6).

The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The protease may also be expressed as a fusion protein, i.e. that the gene encoding the protease has been fused in frame to the gene encoding another protein. This protein may be another enzyme or a functional domain from another enzyme.

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, or a *Streptomyces* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus*, and *Enterococcus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81:823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may be a eukaryote, such as a non-human animal cell, an insect cell, a plant cell, or a fungal cell.

In one particular embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In another particular embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Examples of filamentous fungal host cells are cells of species of, but not limited to, *Acremonium, Aspergillus, Fusarium, Humicola, Mucor, Myceliophthora, Neurospora, Penicillium, Thielavia, Tolypocladium*, or *Trichoderma*.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention comprising (a) cultivating a strain, which in its wild-type form is capable of producing the polypeptide; and (b) recovering the polypeptide. Preferably, the strain is of the genus *Brachysporiella*, such as *Brachysporiella gayana*, or of the genus *Nocardiopsis*, such as *Nocardiopsis dassonvillei* or *Nocardiopsis alba*. Most preferred wild-type strains are: *Nocardiopsis dassonvillei* D SM 43235, *Nocardiopsis alba* D SM 1 5647, *Nocardiopsis prasina* DSM 15649, *Nocardiopsis prasina* DSM 15648, and *Brachysporiella gayana* CGMCC 0865

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence comprising at least one mutation in nucleotides 726-1283 of SEQ ID NO: 13, nucleotides 499-1062 of SEQ ID NO: 11, nucleotides 502-1065 of SEQ ID NO: 9, nucleotides 496-1059 of SEQ ID NO: 7, nucleotides 496-1059 of SEQ ID NO: 5, nucleotides 559-1122 of SEQ ID NO: 3, and/or nucleotides 900-1466 of SEQ ID NO: 1, in which the mutant nucleic acid sequence encodes the corresponding polypeptides which (i) consists of amino acids 1 to 186 of SEQ ID NO: 14, or amino acids 1-188 of any one of (SEQ ID NOs: 12, 10, 8, 6, 4 or 2), or (ii) is a variant of any of the sequences of (i), wherein the variant comprises a substitution, deletion, and/or insertion of one or more amino acids, or (iii) is an allelic variant of any of the sequences of (i), or (iv) is a fragment of any of the sequences of (i).

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a product, or disappearance of a substrate. For example, a protease assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. Nos. 5,689,054 and 6,111,168 are examples of engineered plants.

Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, Plant Physiology 86: 506.

For constitutive expression, the following may be used: The 35S-CaMV promoter may be used (Franck et al., 1980, Cell 21: 285-294), the maize ubiquitin 1 (Christensen AH, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675-689.; Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39:

935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or alterations in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the protease in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are generally preferred for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having protease activity of the present invention under conditions conducive for production of the polypeptide; and (b) recovering the polypeptide.

Animals

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having protease activity of the present invention so as to express and produce the polypeptide. The polypeptide may be recovered from the animal, e.g. from the milk of female animals, or the polypeptide may be expressed to the benefit of the animal itself, e.g. to assist the animal's digestion. Examples of animals are mentioned below in the section headed Animal Feed.

To produce a transgenic animal with a view to recovering the protease from the milk of the animal, a gene encoding the protease may be inserted into the fertilized eggs of an animal in question, e.g. by use of a transgene expression vector which comprises a suitable milk protein promoter, and the gene encoding the protease. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the protease, the transgene may be operably linked to a first regulatory sequence for salivary gland specific expression of the protease, as disclosed in WO 2000064247.

Compositions

In a still further aspect, the present invention relates to compositions comprising a polypeptide of the present invention.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptides or polypeptide compositions of the invention.

Animal Feed

The present invention is also directed to methods for using the protease of the invention in animal feed, as well as to feed compositions and feed additives comprising these polypeptides.

The term animal includes all animals, including human beings. Examples of animals are non-ruminants, and ruminants, such as sheep, goats, horses, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); fish (including but not limited to salmon, trout, tilapia, catfish and carps); and crustaceans (including but not limited to shrimps and prawns).

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may e.g. include other enzymes, in which case it could be termed a protease preparation.

The protease preparation can be (a) added directly to the feed (or used directly in a treatment process of vegetable proteins), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

In a particular embodiment, the protease for use according to the invention is capable of solubilising vegetable proteins. A suitable assay for determining solubilised protein is disclosed in Example 4 of WO 01/58276.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

The treatment according to the invention of vegetable proteins with at least one protease of the invention results in an increased solubilisation of vegetable proteins.

The term solubilisation of proteins basically means bringing protein(s) into solution. Such solubilisation may be due to protease-mediated release of protein from other components of the usually complex natural compositions such as feed. Solubilisation can be measured as an increase in the amount of soluble proteins, by reference to a blank sample with no protease treatment.

In a particular embodiment of a (pre-) treatment process of the invention, the protease(s) in question is affecting (or acting on, or exerting its solubilising influence on) the vegetable proteins or protein sources. To achieve this, the vegetable protein or protein source is typically suspended in a solvent, e.g. an aqueous solvent such as water, and the pH and temperature values are adjusted paying due regard to the characteristics of the enzyme in question. For example, the treatment may take place at a pH-value at which the activity of the actual protease is at least Likewise, for example, the treatment may take place at a temperature at which the activity of the actual protease is at least 40%, 50%, 60%, 70%, 80% or at least 90%. The above percentage activity indications are relative to the maximum activities. The enzymatic reaction is continued until the desired result is achieved, following which it may or may not be stopped by inactivating the enzyme, e.g. by a heat-treatment step.

In another particular embodiment of a treatment process of the invention, the protease action is sustained, meaning e.g. that the protease is added to the vegetable proteins or protein sources, but its solubilising influence is so to speak not switched on until later when desired, once suitable solubilising conditions are established, or once any enzyme inhibitors are inactivated, or whatever other means could have been applied to postpone the action of the enzyme.

In one embodiment the treatment is a pre-treatment of animal feed or vegetable proteins for use in animal feed. The term improving the nutritional value of an animal feed means improving the availability of the proteins, thereby leading to increased protein extraction, higher protein yields, and/or improved protein utilisation. The nutritional value of the feed is therefore increased, and the growth rate and/or weight gain and/or feed conversion (i.e. the weight of ingested feed relative to weight gain) of the animal is/are improved.

The protease can be added to the feed in any form, be it as a relatively pure protease, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the protease of the invention, the animal feed additives of the invention contain at least one fat-soluble vitamin, and/or at least one water soluble vitamin, and/or at least one trace mineral. The feed additive may also contain at least one macro mineral Further, optional, feed-additive ingredients are colouring agents, aroma compounds, stabilisers, antimicrobial peptides, including antifungal polypeptides, and/or at least one other enzyme selected from amongst phytase (EC 3.1.3.8 or 3.1.3.26); xylanase (EC 3.2.1.8);

galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6).

In a particular embodiment these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384. Examples of polyunsaturated fatty acids are C18, C20 and C22 polyunsaturated fatty acids, such as arachidonic acid, docosohexaenoic acid, eicosapentaenoic acid and gamma-linoleic acid. Examples of reactive oxygen generating species are chemicals such as perborate, persulphate, or percarbonate; and enzymes such as an oxidase, an oxygenase or a syntethase.

Usally fat- and water-soluble vitamins, as well as trace minerals form part of a so-called premix intended for addition to the feed, whereas macro minerals are usually separately added to the feed. A premix enriched with a protease of the invention, is an example of an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. In the present context, at least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The above definition of "at least one", by the way, is generally valid all over the present patent application—of course on a by analogy basis, meaning that the upper limit of this definition, in the above example fifteen, of course should reflect the maximum number of choices given in each particular case.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-3.10 g/kg.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N(g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 D A Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 0.5-25, or 5-30, mg enzyme protein per kg animal diet.

The protease should of course be applied in an effective amount, i.e. in an amount adequate for improving solubilisation and/or improving nutritional value of feed. It is at present contemplated that the enzyme is administered in one or more of the following amounts (dosage ranges): 0.01-200; 0.01-100; 0.05-100; 0.5-100; 1-100; 5-100; 10-100; 0.05-50; 1-50; or 0.10-10—all these ranges being in mg protease enzyme protein per kg feed (ppm).

For determining mg enzyme protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg enzyme protein per kg feed is calculated.

The same principles apply for determining mg enzyme protein in feed additives. Of course, if a sample is available of the protease used for preparing the feed additive or the feed, the specific activity is determined from this sample (no need to purify the protease from the feed composition or the additive).

In a particular embodiment, the animal feed additive of the invention is a premix. A premix is usually intended for addition to (inclusion in) animal feed. A typical inclusion rate of premix in feed is 0.01-10.0%, more particularly 0.05-5.0%, or 0.2-1.0%, typically 0.5-1.0%. As the inclusion rate of premix in animal feed varies, it makes sense to describe such premixes with regard to the intended, or prescribed, in-feed-concentrations of the various ingredients.

The premix of the invention contains a protease of the invention, and in addition at least one fat- and/or water-soluble vitamin, and/or at least one trace mineral.

In a particular embodiment, the premix includes, comprises or contains the trace mineral copper, usually in the form of salts of the cupri or cupro ion, i.e. $Cu^{2+}$ or $Cu^+$, respectively, in particular inorganic salts thereof. In particular embodiments of a premix of the invention, the premix contains such an amount of copper (Cu) as to provide, when included in the feed in the prescribed inclusion rate, a concentration in the feed ("in-feed-concentration") of 1-500 ppm copper (ppm meaning, e.g., mg/kg feed).

In further particular embodiments, the in-feed-concentration of copper is below or equal to 5, 10, 20, 25, 50, 60, 70, 80, 90, 100, 110, 120, 130, 140, 150, 200, 300, or below or equal to 400 ppm. On the other hand, the in-feed-concentration of Cu should be at least 0.2, 0.4, 0.6, 0.8, 1.0, 2.0, 3.0, 4.0, or at least 5.0 ppm. Any ranges of in-feed-concentrations using any set of the above indicated upper and lower limits are specifically included herein. Non-limiting examples thereof are 0.2-100, 0.4-100, 0.6-200, 0.8-100, 1-25, 1-50, 1-100, 1-140, 1-150, 2-100, 3-100, 4-100, 5-100, 3-200, 4-200, 5-200, 3-300, 4-300 and 5-5-300 pprn Cu.

The concentration of Cu in the premix as such is of course higher than the intended in-feed-concentration, typically 100-200 times the in-feed-concentration (based on inclusion rates of 1%, and 0.5%, respectively). Therefore, a premix may contain, comprise or include Cu in concentrations of up to 100,000 ppm (200 times an in-feed-concentration of 500 ppm), or even higher. The following are non-limiting examples of maximum in-premix concentrations of Cu: 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000, 70000, 80000, 90000 ppm Cu. The following are non-limiting examples of minimum in-premix concentrations of Cu: 100, 200, 300, 400, 500, 600, 700, 800, 900, 1000, 1100, 1200, 1300, 1400, 1500, 1600, 1700, 1800, 1900, or 2000 ppm Cu. Any ranges of in-premix-concentrations using any set of the above indicated upper and lower limits are specifically included herein. Non-limiting examples thereof are 100-100,000; 200-90,000; 300-80,000; 400-70,000; 500-50,000; 100-10,000; 100-5,000; and 100-2000 ppm Cu.

The following are specific examples of premix compositions of the invention, all of which additionally include a protease of the invention to provide an in-feed concentration of 1-50 mg/kg. The concentrations indicated below of the various other premix components are also in-feed-concentrations (per kg of the feed).

Premix for a piglet diet (complete compound feed): 135 ppm Cu, 100 ppm Zn, 90 ppm Fe, 50 mg Mn, 1.24 ppm I, 0.3 ppm Se, 0.10 ppm Co, 10000 IE/kg vit. A, 2000 IE/kg vit. D3, 90 mg/kg vit. E, 2.25 ppm vit. B1, 3.75 ppm vit. B2, 10.50 ppm vit. B3, 7.5 ppm vit. B6, 0.03 ppm vit. B12, 0.75 ppm vit. K, 0.06 ppm vit. H, 0.9 ppm folic acid, 16.5 ppm niacin.

Premix for another piglet diet: 14400 IE vit. A, 120000 IE vit. D3, 1440 mg vit. E, 2.4 mg vit. B1, 7.2 mg vit. B2, 30 mg niacin, 4.8 mg vit. B6, 48 µg vit. B12, 240 µg biotin, 21.6 mg pantothenic acid, 600 mg cholinchloride, 120 mg Zn, 90 mg Fe, 90 mg Mn, 24 mg Cu, 1.8 mg I, 0.84 mg Co, 0,48 mg Se, 600 mg.

Premix for a third piglet diet: 210 mg of Zn, 246 mg of Fe, 84 mg of Mn, 24 mg of Cu, and 4 mg of I.

Premix for a broiler diet: Retinol, 4.05; cholecalciferol, 0.05; tocopherol, 13.5; menadione, 2.25; thiamin, 1; choline, 375; riboflavin, 5.4; panthothenic acid, 13.5; pyridoxine, 1.1, cyanocobalamin, 0.01; nicotonic acid, 40; biotin, 0.15; 1, 2.1; Co, 1.4; Se, 0.43; Cu, 7.2; Mn, 86; Zn, 57; Fe, 65; Mg, 110.

Premixes for other broiler diets contained 8 or 10 mg Cu/kg diet.

Detergent Compositions

The protease of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease of the invention. The detergent additive as well as the detergent composition may comprise one or more other enzymes such as a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258068 and EP 305216 or from *H. insolens* as described in WO 96/13580, a *Pseudomo-* nas lipase, e.g. from *P. alcaligenes* or *P. pseudoalcaligenes* (EP 218272), *P. cepacia* (EP 331376), *P. stutzeri* (GB 1,372, 034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S).

Suitable amylases (alpha- and/or beta-) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839. Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are DuraMyl™, TermaMyl™, FungaMyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495257, EP 531372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686, 593, U.S. Pat. 5,763,254, WO 95/24471, WO 98/12307 and WO 99/01544. Commercially available cellulases include Celluzyme™, and Carezyme™ (Novozymes A/S), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70 % water and 0-30 % organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65 % of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liqour, preferably 0.05-5 mg of enzyme protein per liter of wash liqour, in particular 0.1-1 mg of enzyme protein per liter of wash liqour.

The enzyme of the invention may additionally be incorporated in the detergent formulations disclosed in WO 97/07202.

Deposit of Biological Material

The following biological materials have been deposited under the terms of the Budapest Treaty with the NRRL (Agricultural Research Service Patent Culture Collection, Northern Regional Research Center), the DSM (Deutsche Sammlung von Mikroorganismen und Zellkulturen GmbH, Mascheroder Weg 1b, 38124 Braunschweig, Germany), and the CGMCC (China General Microbiological Culture Collection Center, Institute of Microbiology, Beijing 100080, China), respectively, and given the following accession numbers:

| Deposit | Accession Number | Date of Deposit |
|---|---|---|
| Nocardiopsis sp. | NRRL 18262 | Nov. 10, 1987 |
| Nocardiopsis prasina | DSM 15648 | May 30, 2003 |
| Nocardiopsis prasina | DSM 15649 | May 30, 2003 |
| Nocardiopsis alba | DSM 15647 | May 30, 2003 |
| Brachysporiella sp. | CGMCC 0865 | Dec. 19, 2002 |
| Escherichia coli | DSM 15509 | Mar. 18, 2003 |

The strain *Nocardiopsis dassonvillei subsp. dassonvillei* DSM 43235 is publicly available from DSM. This strain was also deposited at other depositary institutions as follows: ATCC 23219, IMRU 1250, NCTC 10489. The strain *Nocardiopsis* sp. NRRL 18262 was deposited in connection with the filing of another patent application.

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

The *Brachysporiella* strain CGMCC 0865 was isolated from dead branches of an unidentified plant in China in October 1998. The strains *Nocardiopsis prasina* DSM 15648, *Nocardiopsis prasina* DSM 15649, and *Nocardiopsis alba* DSM 15647 were isolated from soil samples in Denmark in 2001.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Example 1

Proteases

The following proteases were purified using conventional methods from fermentations of the respective wild type strains or recombinant host cells:

Protease 10 (amino acids 1-188 of SEQ ID NO: 2), Protease 18 (amino acids 1-188 of SEQ ID NO: 1 2), the *Brachysporiella* protease (amino acids 1-186 of SEQ ID NO: 14), the *Metarhizium* protease (amino acids 1-188 of SEQ ID NO: 4), Protease 08 (amino acids 1-188 of SEQ ID NO: 10), Protease 11 (amino acids 1-188 of SEQ ID NO: 6), and Protease 35 (amino acids 1-188 of SEQ ID NO: 8).

The purity by SDS-PAGE (see Example 2) of the protease preparations was above 95%, and the Absorption Purity ($A_{280}/A_{260}$ ratio; see Example 3) was above 1.40.

Example 2

Determination of Purity by SDS-PAGE

The purity of the proteases mentioned in Example 1 was determined by SDS-PAGE using the following procedure:

40ul (micro liter) protease solution ($A_{280}$ concentration = 0.025) was mixed with 40 ul 0.1M PMSF in an Eppendorf tube on ice and left for half an hour. Then 20 ul 50% (w/v) TCA (trichloroacetic acid) was added to the Eppendorf tube. After another half an hour on ice the tube was centrifuged (5 minutes, 0° C., 14.000×g) and the supernatant was carefully removed. 20 ul SDS-PAGE sample buffer (200 ul Tris-Glycine SDS Sample Buffer (2×) (125 mM Tris/HCl, pH6.8, 4% (w/v) SDS, 50 ppm bromophenol blue, 20% (v/v) Glycerol, LC2676 from Invitrogen™)+160 ul dist. water+20 ul beta-mercaptoethanol+20 ul 3M unbuffered Tris Base (Sigma T-1503) was added to the precipitate and the tube was boiled for 3 minutes. The tube was centrifuged shortly and 10 ul sample was applied to a 4-20% gradient Tris-Glycine precast gel from Invitrogen™ (polyacrylamide gradient gel based on the Laemmli chemistry but without SDS in the gel, (Laemmli, U. K., (1970) Nature, vol. 227, pp. 680-685), EC60255). The electrophoresis was performed with Tris-Glycine running buffer (2.9 g Tris Base, 14.4 g Glycine, 1.0 g SDS, distilled water to 1 liter) in both buffer reservoirs at a 150V constant voltage until the bromophenol blue tracking dye had reached the bottom of the gel. After electrophoresis, the gel was rinsed 3 times, 5 minutes each, with 100 ml of distilled water by gentle shaking. The gel was then gently shaken with Gelcode® Blue Stain Reagent (colloidal Comassie G-250 product from PIERCE, PIERCE cat. No. 24592) for one hour and washed by gentle shaking for 8 to 16 hours with distilled water with several changes of distilled water. Finally, the gel was dried between 2 pieces of cellophane. Dried gels were scanned with a Arcus II scanner from AGFA equipped with Fotolook 95 v2.08 software and imported to the image evaluation software CREAM™ for Windows (catalogue nos. 990001 and 990005, Kem-En-Tec, Denmark) by the File/Acquire command with the following settings (of Fotolook 95 v2.08): Original=Reflective, Mode=Color RGB, Scan resolution=240 ppi, Output resolution=120lpi, Scale factor=100%, Range=Histogram with Global selection and Min=0 and Max=215, ToneCurve=None, Sharpness=None, Descreen=None and Flavor=None, thereby producing an *.img picture file of the SDS-PAGE gel, which was used for evaluation in CREAM™. The *.img picture file was evaluated with the menu command Analysis/1-D. Two scan lines were placed on the *.img picture file with the Lane Place Tool: A Sample scan line and a Background scan line. The Sample scan line was placed in the middle of a sample lane (with the protease in question) from just below the application slot to just above the position of the bromophenol blue tracking dye. The Background scan line was placed parallel to the Sample scan line, but at a position in the pictured SDS-PAGE gel where no sample was applied, start and endpoints for the Background scan line were perpendicular to the start and endpoints of the Sample scan line. The Background scan line represents the true background of the gel. The width and shape of the scan lines were not adjusted. The intensity along the scan lines where now recorded with the 1-D/Scan menu command with Medium sensitivity. Using the 1-D/Editor menu command, the Background scan was subtracted from the Sample scan. Then the 1-D/Results menu command was selected and the Area % of the protease peak, as calculated by the CREAM™ software, was used as the SDS-PAGE purity of the proteases.

All the protease samples had an SDS-PAGE purity of above 95%.

Example 3

Determination of Absorption Purity

The $A_{280}/A_{260}$ ratio of the purified protease samples was determined as follows.

$A_{260}$ means the absorption of a protease sample at 260 nm in a 1 cm path length cuvette relative to a buffer blank. $A_{280}$ means the absorption of the same protease sample at 280 nm in a 1 cm path length cuvette relative to a buffer blank.

Samples of the purified proteases from Example 1 were diluted in buffer until the $A_{280}$ reading of the spectrophotometer was within the linear part of its response curve. The $A_{280}/A_{260}$ ratio was determined from the readings. The following results were obtained: Protease 10: 1.94, Protease 18: 1.96, *Brachysporiella* protease: 1.48, *Metarhizium* protease: 1.95, Protease 08: 1.86, Protease 11: 1.95, Protease 35: 1.94.

Example 4

Protease Assay—and the Influence of Various Inhibitors on Stability and Activity of Selected Proteases The influence of various potential inhibitors on the activity and stability of the proteases of Example 1 was tested as described below.

Assay buffer 100 mM succinic acid (Merck 1.00682), 100 mM HEPES (Sigma H-3375), 100 mM CHES (Sigma C-2885), 100 mM CABS (Sigma C-5580), 1 mM $CaCl_2$, 150 mM KCl, 0.01% Triton X-100 (Sigma T-9284) adjusted to pH 7.0 with NaOH.

Inhibitors
Fe(II)$SO_4$.7$H_2O$, Sigma F-7002
Cu(II)$SO_4$.5$H_2O$, Merck 2790
Zn(II)$Ac_2$.2$H_2O$, Merck 8802
Mg(II)$Cl_2$.6$H_2O$, Merck 105832
Mn(II)$Cl_2$.2$H_2O$, Merck 5934
Choline chloride, Aldrich C7,970-0 pNA Assay pNA substrate: Suc-AAPF-pNA (Bachem L-1400) or Boc-VLGR-pNA (Bachem L-1205). Temperature: 25° C.

20 ul (micro liter) protease (diluted in 0.01% Triton X-100) was placed in a well of a micro titer plate. The assay was started by adding 200 ul pNA substrate (50 mg dissolved in 1.0 ml DMSO and further diluted 100× with assay buffer). The increase in $OD_{405}$ was monitored as a measure of the protease activity.

Dose/response relationships ($OD_{405}$ min versus (mg enzyme)/l) were determined using the pNA assay for a number of proteases, with and without the various inhibitors. The dose-response curves were linear over a satisfactory broad range of enzyme concentrations. Varying degrees of inhibition were observed: Some proteases included for comparative purposes, viz. porcine trypsin and the SAVINASE™ protease (a subtilisin protease derived from *Bacillus clausii*, commercially available from Novozymes A/S, Krogshoejvej 36, D K-2880 Bagsvaerd, Denmark) were not inhibited, while other proteases were. The addition of inhibitors to already developed yellow p-nitroaniline colour proved to have no effect. It was therefore concluded that the pNA assay was indeed suitable for inhibition measurements.

Stability Assay

The protease was diluted to approx. 1 m g/ml (see below) in assay buffer with 0.1% (w/v) K-sorbate (potassium salt of sorbic acid) and 1 mM inhibitor. The mixture was incubated at 25° C.). At intervals, a sample was withdrawn from the incubation (after thorough mixing) and frozen. After dilution in assay buffer, residual activity was measured using the pNA assay. For the 1 mM inhibitor additions, the incubation was diluted in assay buffer with 5mM EDTA in order to see a pure stability effect.

Protease concentrations were estimated from the theoretical molar extinction coefficients, $E_{280}$ (1M), which can be calculated from the amino acid composition using the formula: $E_{280}(1M)=5690*N_{Trp}+1280*N_{Tyr}+120*N_{Cys}$, where $N_{Trp}$, $N_{Tyr}$, and $N_{Cys}$ are the number of Trp, Tyr, and Cys amino acid residues in the protease (Gill, S. C., von Hippel, P. H., Analytical Biochemistry 182, 319-326, (1989)) and the molecular weight, $M_W$, of the protease calculated from the amino acid sequence. From an $A_{280}$ measurement of a pure protease sample (more than 95% pure according to Example 2), the protease concentration was calculated as: Conc(mg/ml)=$(A_{280}*M_W)/E_{280}(1M))$.

Inhibition Results

The dose/response curves ($OD_{405}$/min versus (mg enzyme)/l) showed no inhibition of any of the proteases by $Fe^{2+}$, $Zn^{2+}$, $Mg^{2+}$, $Mn^{2+}$ or choline chloride (in concentrations of 1mM, added to the assay buffer). $Cu^{2+}$, however, inhibited all of the proteases tested (to a varying extent, as it appears from Table 1 below).

First, the effect of various $Cu^{2+}$ concentrations was tested with an enzyme dosage of 1 mg/l. At least in the range of 0 to 1 mM $Cu^{2+}$ there seemed to be a linear relationship between inhibition and concentration of $Cu^{2+}$, the inhibition manifesting itself as a decrease in the enzyme activity with increasing concentrations of $Cu^{2+}$ (the enzyme activity being measured as average $OD_{405}$ increase/time from the linear part of dose/response curves).

Table 1 shows the activity of the various proteases tested (at enzyme concentrations of 1 mg/l, using a concentration of $Cu^{2+}$ of 1 mM, and using Suc-AAPF-pNA as a substrate, at pH 7 and 25° C.), relative to a control experiment which was identical, except for no $Cu^{2+}$ being added.

TABLE 1

| Enzyme | Enzyme Activity/$mOD_{405}$/min | | Relative Activity |
|---|---|---|---|
| | Control (no $Cu^{2+}$) | +1 mM $Cu^{2+}$ | |
| Protease 10 | 122.2 | 80.3 | 0.657 |
| Protease 18 | 193.1 | 158.0 | 0.818 |
| *Brachysporiella* protease | 72.6 | 50.5 | 0.695 |
| *Metarhizium* protease | 118.2 | 72.4 | 0.612 |
| Protease 08 | 216.0 | 174.5 | 0.808 |
| Protease 11 | 133.6 | 92.3 | 0.691 |
| Protease 35 | 109.2 | 75.0 | 0.687 |

Stability Results

The stability of the various proteases in the presence of the various inhibitors in a concentration of 1 mM was tested as described above. The only inhibitor that had some effect on the stability of some of the proteases was $Cu^{2+}$. However, the effect of this inhibitor was not the same on all the proteases: See the results in Table 2 below showing that Protease 18 and the *Brachysporiella* proteases are indeed stable in the presence of 1 mM $Cu^{2+}$, while the other proteases are not.

TABLE 2

| Enzyme/ Incubation | Residual Enzyme Activity | | | | | | |
|---|---|---|---|---|---|---|---|
| time/hours | 0 | 3.1 | 18.6 | 44.0 | 116.0 | 164.0 | 188.6 |
| Protease 10 | 1.000 | 0.952 | 0.868 | 0.874 | 0.837 | 0.752 | 0.723 |
| Protease 18 | 1.000 | 0.985 | 1.008 | 1.003 | 0.982 | 1.030 | 0.993 |
| *Brachysporiella* protease | 1.000 | 1.022 | 1.073 | 1.057 | 1.029 | 1.053 | 0.984 |
| *Metarhizium* protease | 1.000 | 0.979 | 0.939 | 0.891 | 0.760 | 0.651 | 0.627 |
| Protease 08 | 1.000 | 0.936 | 0.867 | 0.842 | 0.767 | 0.721 | 0.703 |
| Protease 11 | 1.000 | 0.930 | 1.032 | 0.930 | 0.737 | 0.616 | 0.581 |
| Protease 35 | 1.000 | 0.960 | 0.918 | 0.852 | 0.807 | 0.745 | 0.733 |

The invention claimed is:

1. An isolated protease of peptidase family S2A and/or peptidase family S1E, selected from the group consisting of:
   (a) a polypeptide comprising an amino acid sequence which has a degree of identity of at least 90% to amino acids 1-188 of SEQ ID NO: 6 and/or amino acids 1-188 of SEQ ID NO: 8; and
   (b) a fragment of amino acids 1-188 of SEQ ID NO: 6 or 8 which has protease activity.

2. The protease of claim 1, which comprises an amino acid sequence which has a degree of identity of at least 90% to amino acids 1-188 of SEQ ID NO: 6.

3. The protease of claim 1, which comprises an amino acid sequence which has a degree of identity of at least 92% to amino acids 1-188 of SEQ ID NO: 6.

4. The protease of claim 1, which comprises an amino acid sequence which has a degree of identity of at least 95% to amino acids 1-188 of SEQ ID NO: 6.

5. The protease of claim 1, which comprises an amino acid sequence which has a degree of identity of at least 97% to amino acids 1-188 of SEQ ID NO: 6.

6. The protease of claim 1, which comprises the sequence of amino acids 1-188 of SEQ ID NO: 6.

7. The protease of claim 1, which is a fragment of the sequence of amino acids 1-188 of SEQ ID NO: 6.

8. The protease of claim 1, which comprises an amino acid sequence which has a degree of identity of at least 90% to amino acids 1-188 of SEQ ID NO: 8.

9. The protease of claim 1, which comprises an amino acid sequence which has a degree of identity of at least 92% to amino acids 1-188 of SEQ ID NO: 8.

10. The protease of claim 1, which comprises an amino acid sequence which has a degree of identity of at least 95% to amino acids 1-188 of SEQ ID NO: 8.

11. The protease of claim 1, which comprises an amino acid sequence which has a degree of identity of at least 97% to amino acids 1-188 of SEQ ID NO: 8.

12. The protease of claim 1, which comprises the sequence of amino acids 1-188 of SEQ ID NO: 8.

13. The protease of claim 1, which is a fragment of the sequence of amino acids 1-188 of SEQ ID NO: 8.

14. An animal feed additive comprising at least one protease of claim 1 and
   (a) at least one fat soluble vitamin, and/or
   (b) at least one water soluble vitamin, and/or
   (c) at least one trace mineral.

15. The animal feed additive of claim 14, which further comprises Cu in an amount as to provide an in-feed-concentration of Cu of 1-500 ppm.

16. The animal feed additive of claim 14, which comprises Cu in a concentration of up to 100,000 ppm.

17. An animal feed composition having a crude protein content of 50 to 800 g/kg and comprising at least one protease of claim 1.

18. The animal feed composition of claim 17, which further comprises Cu at a concentration of 1-500 ppm.

19. A detergent composition comprising at least one protease of claim 1 and at least one surfactant.

20. An isolated nucleic acid sequence comprising a nucleic acid sequence which encodes the protease of claim 1.

21. A nucleic acid construct comprising the nucleic acid sequence of claim 20 operably linked to one or more control sequences that direct the production of the protease in a suitable expression host.

22. A recombinant expression vector comprising the nucleic acid construct of claim 21.

23. A recombinant host cell comprising the nucleic acid construct of claim 21.

24. A method for producing a protease, comprising
   (a) cultivating a recombinant host cell of claim 23 to produce a supernatant comprising the protease; and
   (b) recovering the protease.

* * * * *

UNITED STATES PATENT AND TRADEMARK OFFICE
CERTIFICATE OF CORRECTION

| | | |
|---|---|---|
| PATENT NO. | : 7,588,926 B2 | Page 1 of 1 |
| APPLICATION NO. | : 10/544861 | |
| DATED | : September 15, 2009 | |
| INVENTOR(S) | : Oestergaard et al. | |

It is certified that error appears in the above-identified patent and that said Letters Patent is hereby corrected as shown below:

On the Title page of the patent, in the list of Foreign Patent documents, delete the first citation "DE 2004328" and insert --DD 2004328--.

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,588,926 B2  Page 1 of 1
APPLICATION NO. : 10/544861
DATED : September 15, 2009
INVENTOR(S) : Oestergaard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 446 days.

Signed and Sealed this

Fourteenth Day of December, 2010

David J. Kappos
*Director of the United States Patent and Trademark Office*